US010095832B2

(12) United States Patent
Van Eijk et al.

(10) Patent No.: US 10,095,832 B2
(45) Date of Patent: Oct. 9, 2018

(54) STRATEGIES FOR HIGH THROUGHPUT IDENTIFICATION AND DETECTION OF POLYMORPHISMS

(71) Applicant: Keygene N.V., Wageningen (NL)

(72) Inventors: Michael Josephus Theresia Van Eijk, Herpen (NL); Henricus Johannes Adam Van Der Poel, Renkum (NL)

(73) Assignee: Keygene N.V., Wageningen (NL)

( * ) Notice: Subject to any disclaimer, the term of this patent is extended or adjusted under 35 U.S.C. 154(b) by 0 days.

(21) Appl. No.: 15/862,956

(22) Filed: Jan. 5, 2018

(65) Prior Publication Data
US 2018/0137241 A1  May 17, 2018

Related U.S. Application Data

(60) Continuation of application No. 15/729,328, filed on Oct. 10, 2017, now Pat. No. 9,898,577, which is a continuation of application No. 15/467,241, filed on Mar. 23, 2017, now Pat. No. 9,898,576, which is a continuation of application No. 15/350,441, filed on Nov. 14, 2016, now Pat. No. 9,896,721, which is a continuation of application No. 14/626,822, filed on Feb. 19, 2015, now Pat. No. 9,493,820, which is a continuation of application No. 14/253,806, filed on Apr. 15, 2014, now Pat. No. 9,023,768, which is a division of application No. 11/993,945, filed as application No. PCT/NL2006/000311 on Jun. 23, 2006, now Pat. No. 8,785,353.

(60) Provisional application No. 60/693,053, filed on Jun. 23, 2005, provisional application No. 60/759,034, filed on Jan. 17, 2006.

(30) Foreign Application Priority Data

Jan. 16, 2006 (EP) .................................. 06075104

(51) Int. Cl.
| | |
|---|---|
| C12P 19/34 | (2006.01) |
| G06F 19/22 | (2011.01) |
| C40B 30/04 | (2006.01) |
| C12Q 1/6827 | (2018.01) |
| C12N 15/10 | (2006.01) |
| C12Q 1/6874 | (2018.01) |
| C12Q 1/6809 | (2018.01) |
| C12Q 1/6806 | (2018.01) |
| C12Q 1/6883 | (2018.01) |
| C12Q 1/6858 | (2018.01) |
| C40B 30/10 | (2006.01) |

(52) U.S. Cl.
CPC ......... *G06F 19/22* (2013.01); *C12N 15/1065* (2013.01); *C12Q 1/6806* (2013.01); *C12Q 1/6809* (2013.01); *C12Q 1/6827* (2013.01); *C12Q 1/6858* (2013.01); *C12Q 1/6874* (2013.01); *C12Q 1/6883* (2013.01); *C40B 30/04* (2013.01); *C12Q 2600/156* (2013.01); *C40B 30/10* (2013.01)

(58) Field of Classification Search
CPC .. C12Q 1/6874; C12Q 1/6827; C12Q 1/6858; C12Q 2525/191; C12Q 2531/113; C12Q 2539/107; C12Q 1/6806; C12Q 1/6809; C12Q 1/6883; C12Q 2600/156; C40B 30/04; C40B 30/10; G06F 19/22; C12N 15/1065
USPC ....................................................... 435/91.2
See application file for complete search history.

(56) References Cited

U.S. PATENT DOCUMENTS

| | | | |
|---|---|---|---|
| 5,759,822 | A | 6/1998 | Chenchik et al. |
| 5,908,978 | A | 6/1999 | Amerson et al. |
| 5,955,276 | A | 9/1999 | Morgante et al. |
| 6,013,445 | A | 1/2000 | Albrecht et al. |
| 6,045,994 | A | 4/2000 | Zabeau et al. |
| 6,090,556 | A | 7/2000 | Kato |
| 6,100,030 | A | 8/2000 | McCasky Feazel et al. |
| 6,232,067 | B1 | 5/2001 | Hunkapiller et al. |
| 6,248,526 | B1 | 6/2001 | Weimer |

(Continued)

FOREIGN PATENT DOCUMENTS

| | | |
|---|---|---|
| EP | 0 534 858 A1 | 3/1993 |
| EP | 0 976 835 | 2/2000 |

(Continued)

OTHER PUBLICATIONS

Fu et al., PNAS, 11(50, 1891-1896, Feb. 4, 2014.*
(Continued)

*Primary Examiner* — Cynthia B Wilder
(74) *Attorney, Agent, or Firm* — Foley & Lardner LLP

(57) ABSTRACT

The invention relates to a method for identifying one or more polymorphisms in nucleic acid samples, comprising: (a) performing a reproducible complexity reduction on a plurality of nucleic acid samples to provide a plurality of libraries of the nucleic acid samples comprising amplified fragments, wherein the reproducible complexity reduction comprises amplifying fragments of the nucleic acid samples using one or more primers to obtain the amplified fragments, and wherein the amplified fragments in each library comprise a unique identifier sequence to indicate origin of each library obtained by the reproducible complexity reduction; (b) combining the plurality of libraries to obtain a combined library and sequencing at least a portion of the combined library to obtain sequences; (c) aligning the sequences to obtain an alignment; and (d) identifying one or more polymorphisms in the plurality of nucleic acid samples.

12 Claims, 12 Drawing Sheets
Specification includes a Sequence Listing.

(56) References Cited

U.S. PATENT DOCUMENTS

| | | |
|---|---|---|
| 6,480,791 B1 | 11/2002 | Strathmann |
| 6,534,293 B1 | 3/2003 | Barany et al. |
| 6,887,666 B1 | 5/2005 | Hager |
| 7,141,364 B1 | 11/2006 | Verma et al. |
| 7,217,516 B2 | 5/2007 | Van Eijk et al. |
| 7,220,549 B2 | 5/2007 | Buzby |
| 7,300,751 B2 | 11/2007 | Li et al. |
| 7,323,305 B2 | 1/2008 | Leamon et al. |
| 7,537,897 B2 | 5/2009 | Brenner et al. |
| 7,935,488 B2 | 5/2011 | Zabeau et al. |
| 8,168,385 B2 | 5/2012 | Brenner |
| 8,614,073 B2 | 12/2013 | Van Eijk et al. |
| 9,376,719 B2 | 6/2016 | Eijk et al. |
| 9,574,230 B2 | 2/2017 | Van Eijk et al. |
| 2002/0025532 A1 | 2/2002 | Huang et al. |
| 2002/0106649 A1 | 8/2002 | Lizardi et al. |
| 2002/0198371 A1 | 12/2002 | Wang |
| 2003/0165923 A1 | 9/2003 | Li et al. |
| 2003/0190645 A1 | 10/2003 | Van Eijk et al. |
| 2003/0207279 A1 | 11/2003 | Crothers et al. |
| 2004/0029155 A1 | 2/2004 | Rothberg et al. |
| 2004/0053236 A1 | 3/2004 | McCallum et al. |
| 2004/0081996 A1 | 4/2004 | Landers et al. |
| 2004/0086912 A1 | 5/2004 | Luo et al. |
| 2004/0101835 A1 | 5/2004 | Willis et al. |
| 2004/0157238 A1 | 8/2004 | Quinn et al. |
| 2004/0185484 A1 | 9/2004 | Costa et al. |
| 2004/0203032 A1 | 10/2004 | Lander et al. |
| 2005/0059065 A1 | 3/2005 | Brenner |
| 2005/0064406 A1 | 3/2005 | Zabarovsky et al. |
| 2005/0095645 A1 | 5/2005 | Jones et al. |
| 2005/0130173 A1 | 6/2005 | Leamon et al. |
| 2005/0153317 A1 | 7/2005 | Denise et al. |
| 2005/0181408 A1 | 8/2005 | Brenner |
| 2005/0233354 A1 | 10/2005 | Kennedy |
| 2006/0177832 A1 | 8/2006 | Brenner |
| 2006/0177833 A1 | 8/2006 | Brenner |
| 2007/0172873 A1 | 7/2007 | Brenner et al. |
| 2008/0032287 A1 | 2/2008 | Cantor et al. |
| 2008/0194418 A1 | 8/2008 | Johnson et al. |
| 2009/0005259 A1 | 1/2009 | Drmanac |
| 2009/0142758 A1 | 6/2009 | Van Eijk et al. |
| 2009/0208943 A1 | 8/2009 | Van Eijk et al. |
| 2014/0051585 A1* | 2/2014 | Prosen ............... B01J 19/0046 506/2 |
| 2014/0303007 A1 | 10/2014 | Van Eijk et al. |
| 2017/0137872 A1 | 5/2017 | Van Eijk et al. |
| 2017/0166962 A1 | 6/2017 | Van Eijk et al. |
| 2017/0206314 A1 | 7/2017 | Van Eijk et al. |
| 2017/0342486 A1 | 11/2017 | Van Eijk et al. |
| 2017/0356042 A1 | 12/2017 | Van Eijk et al. |
| 2018/0002751 A1 | 1/2018 | Van Eijk et al. |

FOREIGN PATENT DOCUMENTS

| | | |
|---|---|---|
| EP | 1 124 990 | 8/2001 |
| EP | 1 362 929 A2 | 11/2003 |
| EP | 1 574 585 | 9/2005 |
| EP | 1 634 956 B1 | 3/2006 |
| JP | 2000-041687 | 2/2000 |
| JP | 2002-537855 | 11/2002 |
| JP | 2004-113241 | 4/2004 |
| JP | 2004-208586 | 7/2004 |
| JP | 2005-021149 | 1/2005 |
| WO | WO-90/008821 A1 | 8/1990 |
| WO | WO-93/06239 | 4/1993 |
| WO | WO-96/04393 | 2/1996 |
| WO | WO-98/51789 | 11/1998 |
| WO | WO-00/24937 A2 | 5/2000 |
| WO | WO-00/24939 | 5/2000 |
| WO | WO-00/53802 | 9/2000 |
| WO | WO-00/61800 A2 | 10/2000 |
| WO | WO-00/61801 | 10/2000 |
| WO | WO-00/78945 | 12/2000 |
| WO | WO-01/21840 A2 | 3/2001 |
| WO | WO-01/38572 | 5/2001 |
| WO | WO-01/75167 A1 | 10/2001 |
| WO | WO-01/88189 | 11/2001 |
| WO | WO-03/012118 | 2/2003 |
| WO | WO-2004/022758 | 3/2004 |
| WO | WO-2004/057017 | 7/2004 |
| WO | WO-2004/063323 | 7/2004 |
| WO | WO-2005/003375 A2 | 1/2005 |
| WO | WO-2005/065814 | 7/2005 |
| WO | WO-2006/137733 A | 12/2006 |
| WO | WO-2006/137734 | 12/2006 |

OTHER PUBLICATIONS

Illumina (Data Sheet: Sequencing), www.illumina.com, Pub. No. 770-2012-019, pp. 1-3, first published 2012. current as of Nov. 17, 2014.*

Miner "Molecular barcodes detect redundancy and contamination in hairpin-bisulfite PCR", Nucleic Acids Research, 2004, vol. 32, No. 17, 4 pages.

U.S. Appl. No. 90/013,467, filed Mar. 13, 2015, Cornell University.

Altshuler, et al. "An SNP map of the human genome generated by reduced representation shotgun sequencing", Nature, Sep. 28, 2000, vol. 47, pp. 513-516.

Bishop, et al. "Analysis of the transcriptome of the protozoan Theileria parva using MPSS reveals that the majority of genes are transcriptionally active in the schizont stage", Nucleic Acids Research, 2005, vol. 33, No. 17, pp. 5503-5511.

Dong, et al. "Flexible Use of High-Density Oligonucleotide Arrays for Single-Nucleotide Polymorphism Discovery and Validation", Genome Research, 2001, vol. 11, No. 8, pp. 1418-1424.

EP Search Report in EP Appln No. 10 18 4351 dated Jan. 28, 2011.

Gupta, et al. "Single nucleotide polymorphisms: A new paradigm for molecular marker technology and DNA polymorphism detection with emphasis on their use in plants", Current Science, Feb. 25, 2001, vol. 80, No. 4 pp. 524-535.

International Search Report in PCT/NL2006/000312 dated Sep. 28, 2006.

Iwahana, et al. "T-cassette Ligation: A Method for Direct Sequencing and Cloning of PCR-amplified DNA Fragments", PCR Methods and Applications, 1994, pp. 219-224.

Jordan, et al. "Genome complexity reduction for SNP genotyping analysis", PNAS, Mar. 5, 2002, vol. 99, No. 5, pp. 2942-2947.

Lehninger, "The Principles of Biochemistry", The Johns Hopkins University School of Medicine, Nov. 1982, Table of Contents.

Margulies, et al. "Genome sequencing in microfabricated high-density picolitre reactors", Nature, Sep. 15, 2005, vol. 437, No. 7057, pp. 376-380.

Matsuzaki, et al. "Parallel Genotyping of Over 10,000 SNPs Using a One-Primer Assay on a High-Density Oligonucleotide Array" Genome Research (Mar. 2004) vol. 14, No. 3, pp. 414-425.

Meksem, et al. "Conversion of AFLP bands into high-throughput DNA markers", MGG—Molecular Genetics and Genomics, Apr. 2001, vol. 265, No. 2, pp. 207-214.

Meyers, et al. "Analysis of the transcriptional complexity of *Arabidopsis thaliana* by massively parallel signature sequencing", Nature Biotechnology, Aug. 2004, vol. 22, No. 8, pp. 1006-1011.

Mueller, et al. "AFLP genotyping and fingerprinting", Tree (Oct. 1999), vol. 14, No. 10, pp. 389-394.

Nicod, et al. "SNPs by AFLP (SBA): a rapid SNP isolation strategy for non-model organisms", Nucleic Acids Research, 2003, vol. 31, No. 5, e19, 5 pgs.

Office Action in JP Appln No. 2008-518056 dated Jun. 27, 2012.

Office Action in JP Appln No. 2013-006095 dated Jul. 2, 2014.

Partial EP Search Report in EP Appln No. 10 07 5564 dated Feb. 8, 2011.

Rafalski "Applications of single nucleotide polymorphisms in crop genetics", Current Opinion in Plant Biology (2002) vol. 5, pp. 94-100.

Volkmuth, et al. "Technical Advances: Genome-Wide cDNA-AFLP Analysis of the *Arabidopsis* Transcriptome", A Journal of Integrative Biology, 2003, vol. 7, No. 2, pp. 143-160.

(56) References Cited

OTHER PUBLICATIONS

Vos, et al., "AFLP: a new technique for DNA fingerprinting", Nucleic Acids Research, 1995, vol. 23, No. 21, pp. 4407-4414.
Yuanxin, et al. "T-linker-specific ligation PCR (T-linker PCR): an advanced PCR technique for chromosome walking or for isolation of tagged DNA ends", Nucleic Acids Research, 2003, vol. 31, No. 12, e68, 7 pgs.
"Instruction Manual AFLP Analysis System 1-7 II AFLP Small Genome Primer Kit", Jan. 22, 2003, retrieved from URL: https://nature.berkeley.edu/brunslab/ftp/aflpii.pdf.
454 Life Science, "Keygene Selects 454 Life Sciences' Novel Sequencing Technology to Enable Large-Scale SNP Discovery and Detection in Higher Eukaryotic Organisms," News & Events—Press Releases, 2006, pp. 1-2, [XP002452166], Internet: URl:http://www.454.com/news-events/press-releases.asp?display=detail&id=46.
Amos, Cl. et al., "DNA Pooling in Mutation Detection with Reference to Sequence Analysis", American Journal of Human Genetics, vol. 66, 2000, pp. 1689-1692.
Baird, et al. "Rapid SNP Discovery and Genetic Mapping Using Sequenced RAD Markers", PLoS One, Oct. 2008, vol. 3, Issue 10, e3376, pp. 1-7.
Bensch, et al. "Ten years of AFLP in ecology and evolution: why so few animals?", Molecular Ecology, Sep. 2005, vol. 14, Issue 10, pp. 2899-2914.
Bouzidi, et al., "A sunflower BAC library suitable for PCR screening and physical mapping of targeted genomic regions.", TAG, vol. 113, No. 1, 2006, pp. 81-89.
Brenner, et al., "DNA fingerprinting by sampled sequencing", Proc. Natl. Acad. Sci., Nov. 1989, vol. 86, pp. 8902-8906.
Breyne, et al. "Transcriptome analysis during cell division in plants", PNAS, Nov. 12, 2002, vol. 99, No. 23, pp. 14825-14830.
Church, et al., "Multiplex DNA Sequencing", Research Articles, Science, vol. 240, Apr. 1988, pp. 185-188.
Colbert, T. et al., "High-Throughput Screening for Induced Point Mutations", Plant Physiology (2001) vol. 126, pp. 480-484.
Data sheet DraI, download from the internet, http://www.neb.com/nebecomm/products, printed on Dec. 18, 2010, p. 1.
Duprat et al., "The *Arabidopsis* eukaryotic initiation factor (iso) 4E is dispensable for plant growth but required for susceptibility to potyviruses", The Plant Journal, 2002, vol. 32, pp. 927-934.
Epinat et al., "A novel engineered meganuclease induces homologous recombination in yeast and mammalian cells", Nucleic Acids Research, 2003, vol. 31, No. 11, pp. 2952-2962.
Fakhrai-Rad, H. et al., "Pyrosequencing: An Accurate Detection Platform for Single Nucleotide Polymorphisms", Human Mutation, vol. 19, pp. 479-485 (2002).
Fujiki et al., "Genetic evidence for CFTR dysfunction in Japanese: background for chronic pancreatitis" (2004) J Med Genet, 41, e55, pp. 1-6.
Greene et al., "Spectrum of chemically induced mutations from a large-scale reverse-genetic screen in *Arabidopsis*", Genetics, Jun. 2003, vol. 164, pp. 731-740.
Gregory, et al., "Genome Mapping by Fluorescent Fingerprinting", Genome Research, 1997, vol. 7, pp. 1162-1168.
Griffin, et al. "Single-nucleotide polymorphism analysis by MALDI-TOF mass spectrometry", TIBTECH, Feb. 2000, vol. 18, pp. 77-84.
Gruber, et al., "Estimation of single nucleotide polymorphism allele frequency in DNA pools by using Pyrosequencing", Hum Genet (2002), vol. 110, pp. 395-401.
Havre et al., "Targested mutagenesis of DNA using triple helix-forming oligonucleotides linked to psoralen", Proc. Natl. Acad. Sci, Aug. 1993, vol. 90, pp. 7879-7883.
Henikoff, et al. "TILLING. Traditional Mutagenesis Meets Functional Genomics", Plant Physiology, Jun. 2004, vol. 135, pp. 630-636.
Hug et al., "Measurement of the number of molecules of a single mRNA species in a complex mRNA preparation", J. theor. Biol., 2003, vol. 221, pp. 615-624.

Jamsari, et al., "BAC-derived diagnostic markers for sex determination in asparagus.", Theoretical and Applied Genetics, vol. 108, No. 6, 2004, pp. 1140-1146.
Janssen, et al., "Application of Corps? Technology for SNP Marker Discovery in Maize," Plant & Animal Genomes XV Conference, 2007, p. 1 [XP002452171], Internet: URL:http://www.intl-pag.org/15/abstracts/PAG15_PO3e_183.html.
Klein, et al., "A high-throughput AFLP-based method for constructing integrated genetic and physical maps: Progress toward a sorghum genome map", Genome Research, vol. 10, No. 5, 2000, pp. 789-807.
Lavebratt, et al., "Pyrosequencing-Based SNP Allele Frequency Estimation in DNA Pools", Human Mutation, vol. 23, pp. 92-97 (2004).
Lewis, et al. "High-Density Detection of Restriction-Site-Associated DNA Markers for Rapid Mapping of Mutated Loci in Neurospora", Genetics, Oct. 2007, vol. 177, pp. 1165-1171.
Li et al., "A fast neutron deletion mutagenesis-based reverse genetics system for plants", The Plant Journal, 2001, vol. 27, No. 3, pp. 235-242.
Lindstedt, et al. "A variation fo the amplified-fragment length polymorphism (AFLP) technique using three restriction endonucleases, and assessment of the enzyme combination BgIII-MfeI for AFLP analysis of *Salmonella enterica* subsp. *enterica* isolates", FEMS Microbiology Letters, 2000, vol. 189, pp. 19-24.
Lizardi, et al. "Mutation detection and single-molecule counting using isothermal rolling-circle amplification", Nature Genetics, Jul. 1998, vol. 19, pp. 225-232.
Lloyd et al., "Targeted mutagenesis using zinc-finger nucleases in *Arabidopsis*", PNAS, Feb. 8, 2005, vol. 102, No. 6, pp. 2232-2237.
Marra, et al., "High Throughput Fingerprint Analysis of Large-Insert Clones", Genome Research, 1997, vol. 7, pp. 1072-1084.
Marth, et al. "A general approach to single-nucleotide polymorphism discovery", Nature Genetics, Dec. 1999, vol. 23, pp. 452-456.
McCallum et al., "Targeting Induced LocalLesions INGenomes (TILLING) for Plant Functional Genomics", Plant Physiology (2000), vol. 123, No. 2, pp. 439-442.
McCallum, et al., "Targeted Screening for Induced Mutations", Nature Biotechnology (Apr. 2000), vol. 18, No. 4, pp. 455-457.
Meissner et al., "Reduced representation bisulfite sequencing for comparative high-resolution DNA methylation analysis", Nucleic Acids Research, 2005, vol. 3, No. 18, pp. 5868-5877.
Menda et al., "In silico screening of a saturated mutation library of tomato", The Plant Journal, 2004, vol. 38, pp. 861-872.
Miller et al., "A comprehensive approach to clustering of expressed human gene sequence: the sequence tag alignment and consensus knowledge base", Genome Research, 1999, vol. 9, pp. 1143-1155.
Miller, et al. "RAD marker microarrays enable rapid mapping of zebrafish mutations", Genome Biology, 2007, vol. 8, Issue 6, Article R105, 10 pages.
Miller, et al. "Rapid and cost-effective polymorphism identification and genotyping using restriction site associated DNA [RAD] markers", Genome Research, 2007, vol. 17, pp. 240-248.
Nair, et al. "PCR-based DNA markers linked to a gall midge resistance gene, Gm4t, has potential for marker-aided selection in rice", Theor Appl Genet (1996), vol. 92, pp. 660-665.
Nakai, et al. "Highly Multiplexed Genotyping of Coronary Artery Disease-Associated SNPs Using MALDI-TOF Mass Spectrometry", Human Mutation, 2002, vol. 20, pp. 133-138.
Nelson, et al. "Complete Genome Sequence of the Oral Pathogenic Bacterium Porphyromonas gingivalis Strain W83", Journal of Bacteriology, Sep. 2003, pp. 5591-5601.
Nicaise et al., "The eukaryotic translation initiation factor 4E controls lettuce susceptibility to the potyvirus Lettuce mosaic virus1", Plant Physiology, Jul. 2003, vol. 132, pp. 1272-1282.
Qiu, F. et al., "DNA Sequence-Based 'Bar Codes' for Tracking the Origins of Expressed Sequence Tags from a Maize cDNA Library Constructed Using Multiple mRNA Sources", Plant Physiology, 133:475-481, Oct. 2003.
Reijans, et al. "Quantitative comparison of cDNA-AFLP, microarrays, and GeneChip expression data in *Saccharomyces cerevisiae*", Genomics, 2003, vol. 82, pp. 606-618.

(56) References Cited

OTHER PUBLICATIONS

Retrieved from EBI accession No. UNIPROT:C5Z1D0, Sep. 1, 2009, "RecName: Full=Pectinesterase; EC=3.1.1.11;".
Retrieved from EBI accession No. UNIPROT:Q8VYZ3, Mar. 1, 2002, "RecName: Full=Probable pectinesterase 53; Short=PE 53; EC=3.1.1.11; AltName: Full=Pectin methylesterase 53; short-AtPME53; Flags: Precursor;".
Ruffel et al., "A natural recessive resistance gene against potato virus Y in pepper corresponds to the eukaryotic initiation factor 4E (eIF4E)", The Plant Journal, 2002, vol. 32, pp. 1067-1075.
Ruffel et al., "The recessive potyvirus resistance gene pot-1 is the tomato orthologue of the pepper pvr2-eIF4E gene" Mol.Gen. Genetics, 2005, vol. 274, pp. 346-353.
Sallaud, et al. "Highly efficient production and characterization of T-DNA plants for rice (Oryza sativa L.) functional genomics", Theor Appl Genet, 2003, vol. 106, pp. 1396-1408.
Savelkoul, et al. "Amplified-Fragment Length Polymorphism Analysis: the State of an Art", Journal of Clinical Microbiology, 1999, vol. 37, No. 10, pp. 3083-3091.
Shendure et al., "Accurate multiplex polony sequencing of an evolved bacterial genome" Science, Sep. 9 2005, vol. 309, pp. 1728-1732.
Simko, I. "One potato, two potato: haplotype association mapping in autotetraploids", Trends in Plant Science, vol. 9, No. 9, Sep. 2004, p. 441-448.
Solexa, "Application Note: DNA sequencing," 2006, pp. 1-2, [XP002452169], Internet: URL:http://www.fasteris.com/pdf/DNASeq_AppNote_10_5_06.pdf.
Sood, et al., Method for reverse genetic screening in zebrafish by resequencing and TILLING, Methods, vol. 29, 2006, pp. 220-227.
Stemple, D.L., "TILLING—a high-throughput harvest for functional genomics", Nature Reviews 1 Genetics, vol. 5, pp. 1-6 (Feb. 2004).
Stewart et al., "A rapid CTAB DNA isolation technique useful for RAPD fingerprinting and other PCR applications" Biotechniques, 1993, vol. 14, No. 5., pp. 748-750.
Swindell, "The Association Among Gene Expression Responses to Nine Abiotic Stress Treatments in *Arabidopsis thaliana*", Genetics, Dec. 2006, vol. 1811-1824.
Till, et al. "Large-scale discovery of induced point mutations with high-throughput TILLING." Genome Research, Mar. 2003, vol. 13, No. 3, pp. 524-530.
Truong et al, "Sequence-Based Genotyping for Marker Discovery and Co-Dominant Scoring in Germplasm and Populations," May 2012, PLoS ONE, vol. 7, No. 5, e37565, pp. 1-9.
Van Der Meulen, et al. "Highly automated AFLP fingerprint analysis on the MegaBACE capillary sequencer", Plant, Animal & Microbe Genomes X Conference, Jan. 12-16, 2002, P228, pp. 135.
van Eijk, et al., "Complexity Reduction of Polymorphic Sequences (CRoPS): A Novel Approach for High Throughput Polymorphism Discovery," Plant and Animal Genomes XIV Conference, 2006, p. 1, [XP002452165], Internet: URL:http://www.intl-pag.org/14/abstracts/PAG14_W410.html.
van Eijk, et al., "Sequence-Based AFLP® Detection Using Solexa's Clonal Single Molecule Array (CSMA?) Technology," Plant & Animal Genomes XV Conference, 2007, p. 1, [XP002452170], Internet: URL:http://www.intl-pag.org/15/abstracts/PAG15_P02c_69.html.
Van Orsouw et al., "Complexity reduction of polymorphic sequences (CRoPS (TM)): A novel approach for large-scale polymorphism discovery in complex genomes", PLoS One, Nov. 2007, vol. 2, No. 11, pp. e1172-e1172, 10 pages.
Vandenbussche, et al. "Toward the analysis of the petunia MADS box gene family by reverse and forward transposon insertion mutagenesis approaches: B, C, and D floral organ identify functions require SEPALLATA-like MADS box genes in petunia." The Plant Cell, Nov. 2003, vol. 15, No. 11, pp. 2680-2693.
Vieux, E. F. et al., "Primer Design for PCR and Sequencing in High-Throughput Analysis of SNPs", BioTechniques, vol. 32, pp. S28-S32 (2002).
Wienholds, et al. "Efficient Target-selected mutagenesis in zebrafish." Genome Research, (2003) vol. 13, No. 12, pp. 2700-2707.
Wienholds, et al. "Target-selected gene inactivation in zebrafish", Methods in Cell Biology, 2004, Chapter 4, vol. 77, pp. 69-90.
Wienholds, et al. "Target-Selected Inactivation of the Zebrafish rag1 Gene", Science (2002), vol. 297, pp. 99-102.
Wolford, et al., "High-throughput SNP detection by using DNA pooling and denaturing high performance liquid chromatography (DHPLC)", Human Genetics (2000) vol. 107, pp. 83-487.
World's Technology News, "Solexa to Conduct Technology Seminar at the American Society of Human Genetics Conference", 2005, p. 1, [XP002452168], Internet: URL:http://www.mirror99.com/20051028/solexa_to_conduct_technology_seminar_at_the_american_society_of_human_genetics_bhfd.jspx.
Xia, et al., "Construction and characterization of a BAC library of soybean.", vol. 141, No. 1-2, 2005, pp. 129-137.

\* cited by examiner

Figure 1A
Primer set I used for preamplification of PSP-11
    E01LKRS1 5'-CGTCAGACTGCGTACCAATTCA-3' (SEQ ID NO:1)
    M15KKRS1 5'-TGGTGATGAGTCCTGAGTAACA-3' (SEQ ID NO:2)
Primer set II used for preamplification of PI20234
    E01LKRS2 5'-CAAGAGACTGCGTACCAATTCA-3' (SEQ ID NO:3)
    M15KKRS2 5'-AGCCGATGAGTCCTGAGTAACA-3' (SEQ ID NO:4)
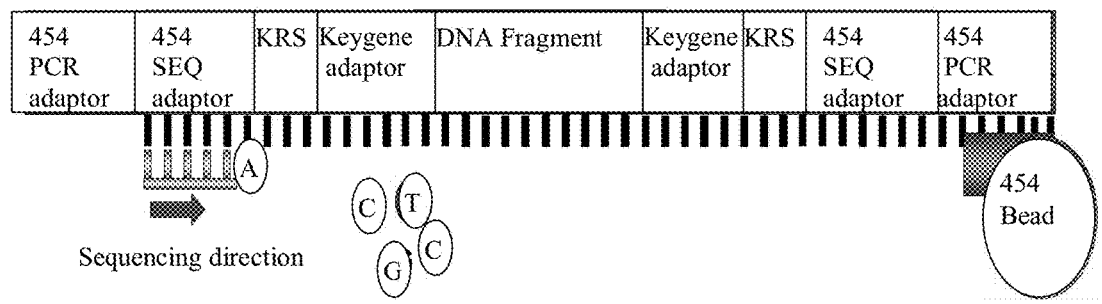
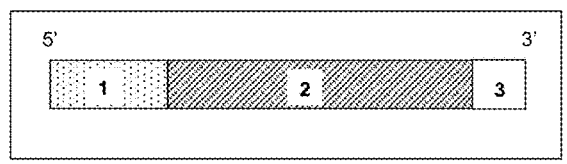
Figure 1B DNA quality control on a 1% agarose gel
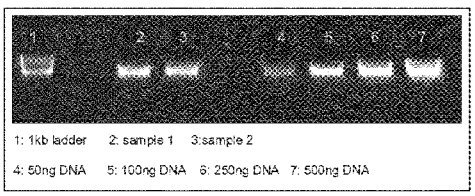
1: 1kb ladder   2: sample 1   3: sample 2
4: 50ng DNA   5: 100ng DNA   6: 250ng DNA   7: 500ng DNA
Figure 2A. Short gel electrophoresis
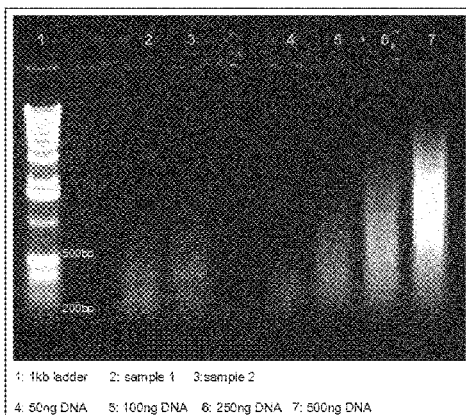
1: 1kb ladder   2: sample 1   3: sample 2
4: 50ng DNA   5: 100ng DNA   6: 250ng DNA   7: 500ng DNA
Figure 2B. Long gel electrophoresis
DNA concentration measured with the Nanodrop
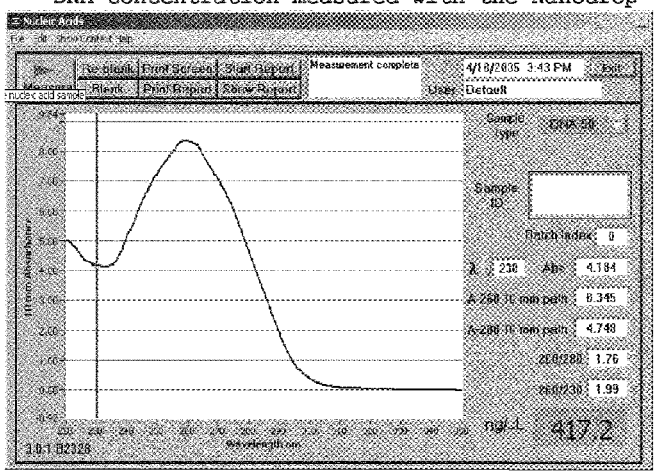
Figure 2C. Concentration sample 1.
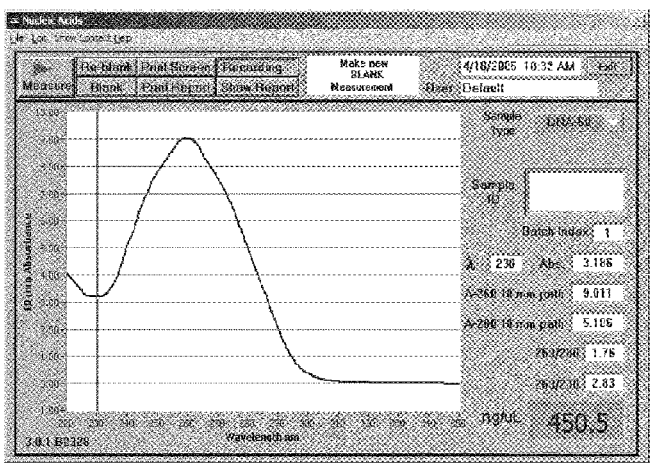
Figure 2D. Concentration sample 2

DNA quality control on a 1% agarose gel
DNA concentrations measured on the Nanodrop
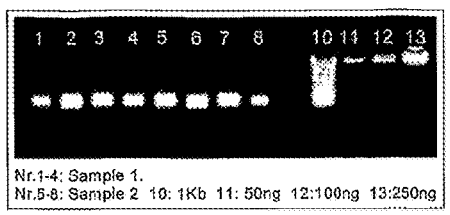
Nr.1-4: Sample 1.
Nr.5-8: Sample 2  10: 1Kb  11: 50ng  12:100ng  13:250ng
Figure 3A. Short gel electrophoresis
| Nr. | Sample ID | ng/uL | A260 | 260/280 | 260/230 | Constant |
|---|---|---|---|---|---|---|
| 1 | P1.1 | 22.61 | 0.452 | 1.5 | 1.81 | 50 |
| 2 | P1.2 | 19.08 | 0.382 | 1.67 | 2.49 | 50 |
| 3 | P1.3 | 18.05 | 0.361 | 1.03 | 2.35 | 50 |
| 4 | P1.4 | 15.19 | 0.304 | 1.71 | 2.1 | 50 |
| Nr. | Sample ID | ng/uL | A260 | 260/280 | 260/230 | Constant |
|---|---|---|---|---|---|---|
| 5 | P2.1 | 17.5 | 0.35 | 1.66 | 2.01 | 50 |
| 6 | P2.2 | 16.67 | 0.333 | 1.96 | 2 | 50 |
| 7 | P2.3 | 22.03 | 0.441 | 1.81 | 2.28 | 50 |
| 8 | P2.4 | 9.8 | 0.196 | 1.78 | 1.98 | 50 |
Figure 3C.
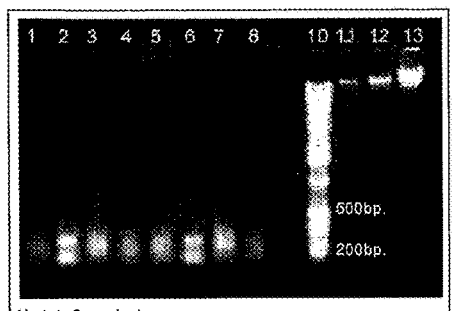
Nr.1-4: Sample 1.
Nr.5-8: Sample 2  10: 1Kb  11: 50ng  12:100ng  13:250ng
Figure 3B. Long gel electrophoresis Figure 4A. Sequence data processing pipeline
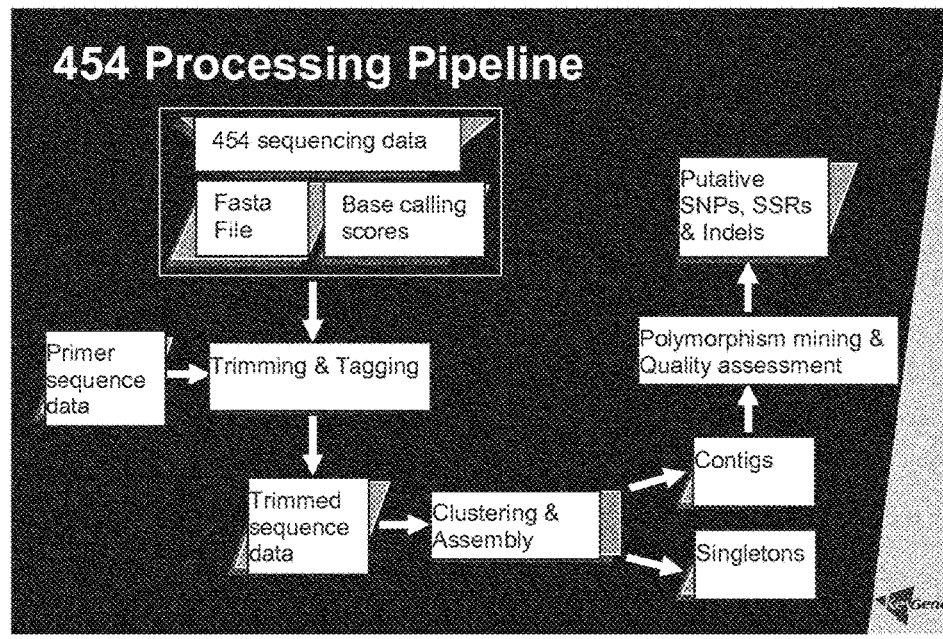
Figure 4B. Polymorphism mining and quality assignment process
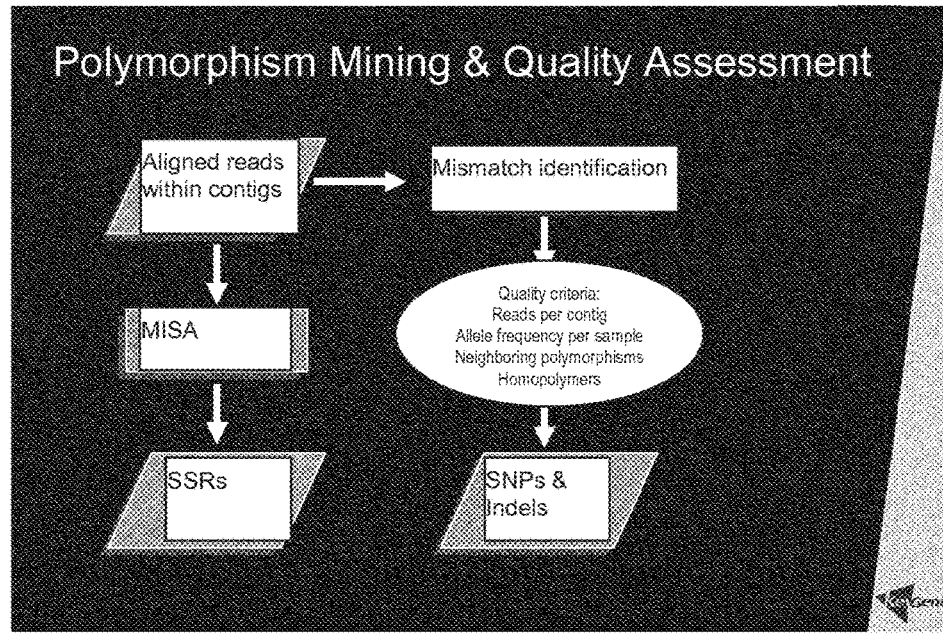

FIG 5A

Panel 1: Example of a mixed tag

(SEQ ID NO: 48)
CAAGAGACTGCGTACCAATTCAACTTTGAGGTGAAAGATCGAAGGTTGCA
CAAGAGACTGCGTACCAATTCA (ES2) (SEQ ID NO: 12)

(SEQ ID NO: 49)
AACACCAAGTGGCCGACCATCTCTTGCGTGTTACTCAGGACTCATCACCAC
(SEQ ID NO: 50) (MS1) TGTTACTCAGGACTCATCACCA

Panel 2: Overview of observed fragments containing expected tags and mixed tags

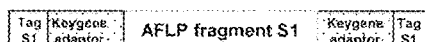 Expected S1-S1

+

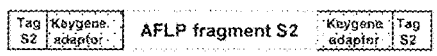 Expected S2-S2

+

Observed but not expected S1-S2 & S2-S1

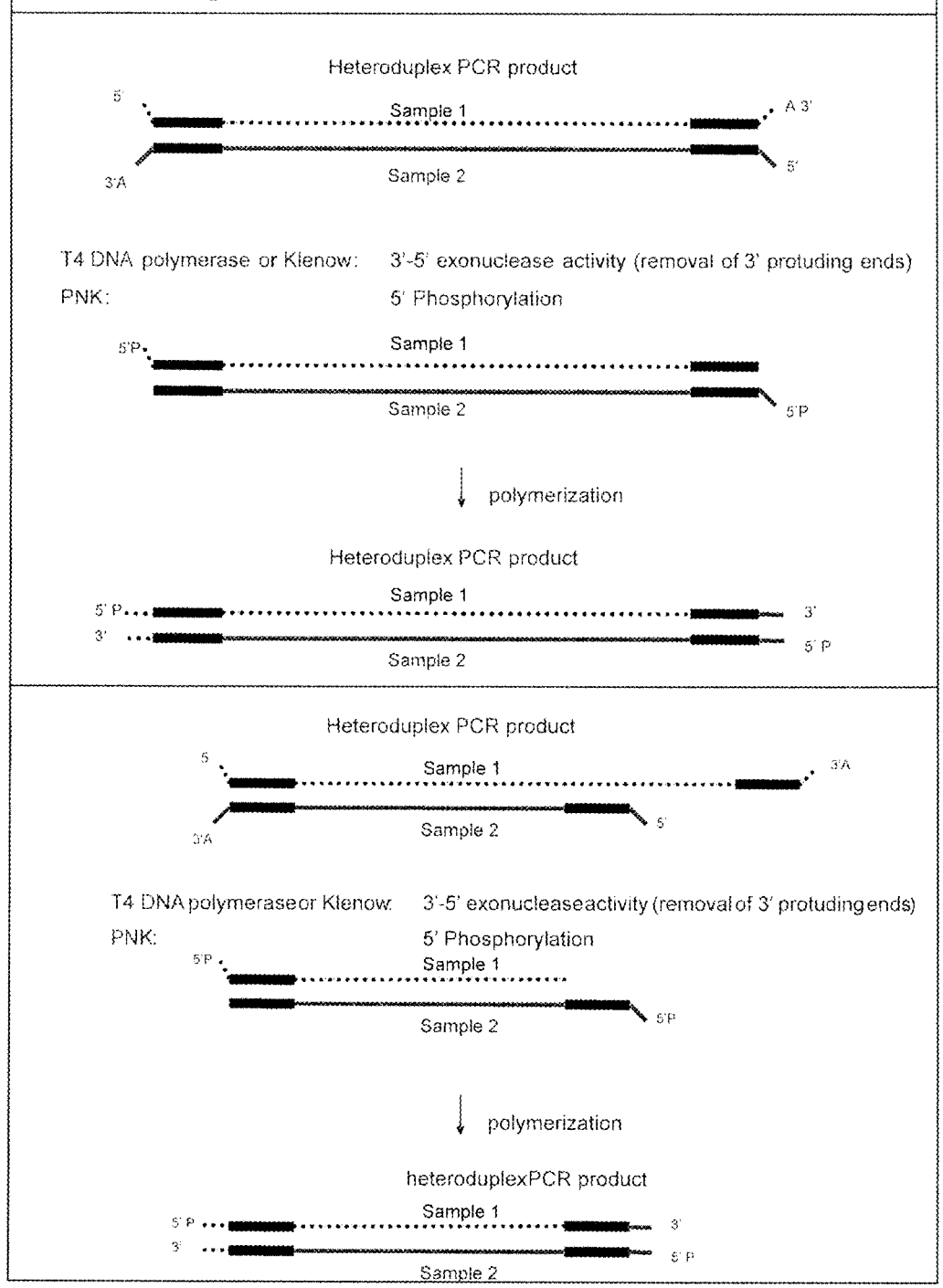

FIG 6A

Panel 1: Example of a concatamer

(SEQ ID NO: 51)
TGGTGATGAGTCCTGAGTAACGGGCCTTTCTTTGTACACT
TGGTGATGAGTCCTGAGTAACA (MS1) (SEQ ID NO: 52)

(SEQ ID NO: 53)                                    (SEQ ID NO: 54)
TGAATTGGTACGCAGTCTGACG|AGCCGATGAGTCCTGAGTAACA
TGAATTGGTACGCAGTCTGACG|AGCCGATGAGTCCTGAGTAACA
(SEQ ID NO: 53)         (ES1) | (MS2)         (SEQ ID NO: 54)

TAAAGGTAAAGCGTGAATTGGTACG(SEQ ID NO: 55)
                TGAATTGGTACGCAGTCTCTTG (ES2) (SEQ ID NO: 56)

Panel 2: Overview of observed fragments containing expected tags and concatamers

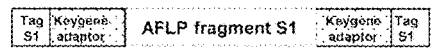 Expected S1-S1

+

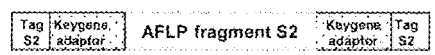 Expected S2-S2

+

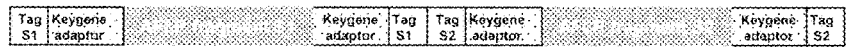

Observed but not expected S1-S1-S2-S2

FIG 6B
| Panel 3: Hypothesized solution to avoid generation of concatamers and mixed tags |
|---|
Regular adaptor
Modified adaptor

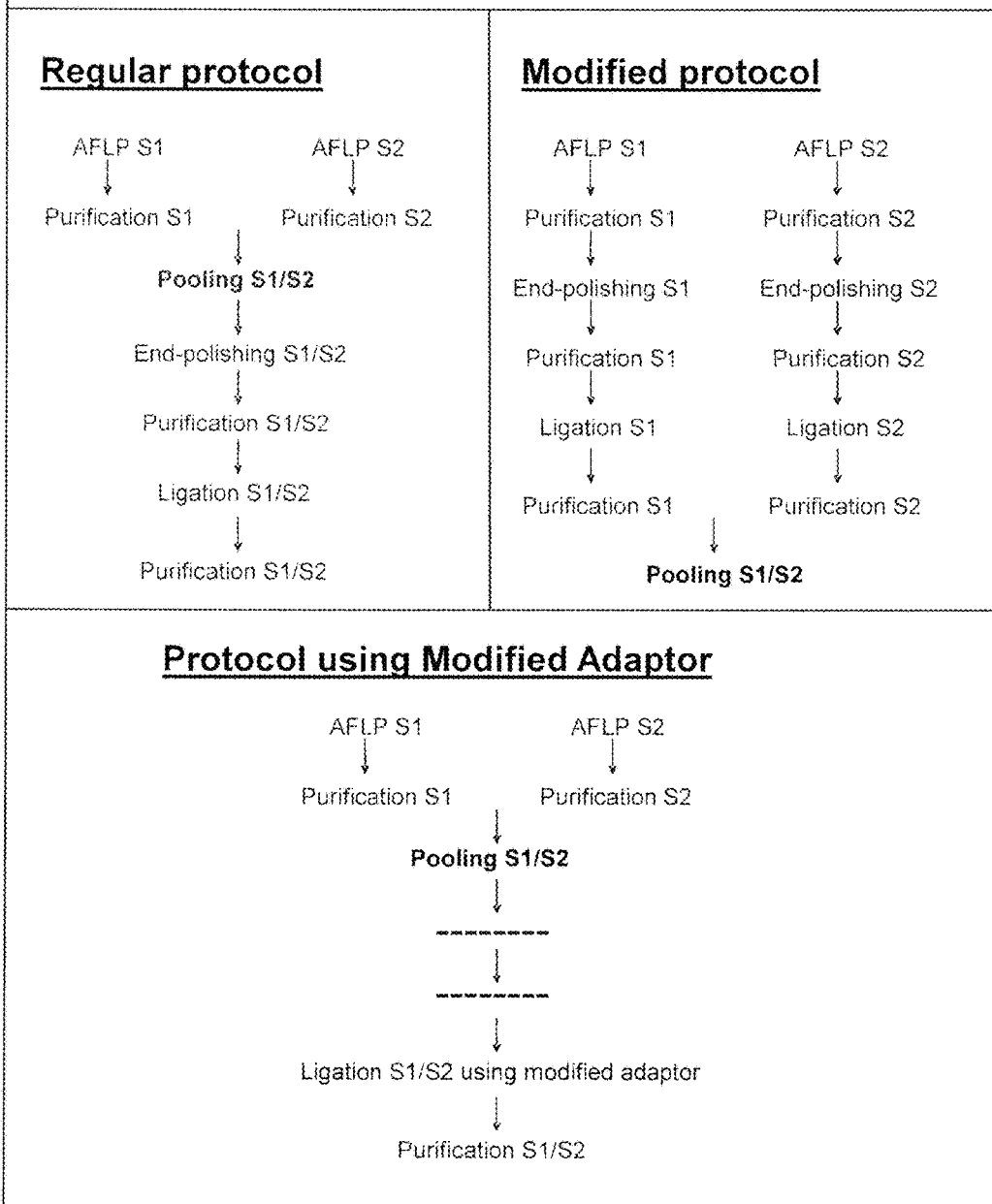

FIG. 7

STRATEGIES FOR HIGH THROUGHPUT IDENTIFICATION AND DETECTION OF POLYMORPHISMS

CROSS-REFERENCE TO RELATED APPLICATIONS

This application is a Continuation Application of U.S. patent application Ser. No. 15/729,328, filed Oct. 10, 2017, which is a Continuation Application of U.S. patent application Ser. No. 15/467,241, filed Mar. 23, 2017, which is a Continuation Application of U.S. patent application Ser. No. 15/350,441, filed Nov. 14, 2016, which is a Continuation Application of U.S. patent application Ser. No. 14/626,822, now U.S. Pat. No. 9,493,820, which is a Continuation Application of U.S. patent application Ser. No. 14/253,806, now U.S. Pat. No. 9,023,768, which is a Divisional Application of U.S. patent application Ser. No. 11/993,945, now U.S. Pat. No. 8,785,353, which is a National Stage entry of International Patent Application No. PCT/NL2006/000311, filed Jun. 23, 2006, which claims benefit under 35 U.S.C. § 119(e) of U.S. Provisional Application Nos. 60/693,053, filed Jun. 23, 2005 and 60/759,034, filed Jan. 17, 2006 and which also claims priority to European Application No. 06075104.7, filed Jan. 16, 2006. Each of these applications is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jan. 5, 2018, is named 085342-1304SequenceListing.txt and is 18 KB in size.

TECHNICAL FIELD

The present invention relates to the fields of molecular biology and genetics. The invention relates to rapid identification of multiple polymorphisms in a nucleic acid sample. The identified polymorphisms may be used for development of high-throughput screening systems for polymorphisms in test samples.

BACKGROUND OF THE INVENTION

Exploration of genomic DNA has long been desired by the scientific, in particular medical, community. Genomic DNA holds the key to identification, diagnosis and treatment of diseases such as cancer and Alzheimer's disease. In addition to disease identification and treatment, exploration of genomic DNA may provide significant advantages in plant and animal breeding efforts, which may provide answers to food and nutrition problems in the world.

Many diseases are known to be associated with specific genetic components, in particular with polymorphisms in specific genes. The identification of polymorphisms in large samples such as genomes is at present a laborious and time-consuming task. However, such identification is of great value to areas such as biomedical research, developing pharmacy products, tissue typing, genotyping and population studies.

SUMMARY OF THE INVENTION

The present invention provides for a method of efficiently identifying and reliably detecting polymorphisms in a complex, e.g. very large, nucleic acid sample (e.g. DNA or RNA) in a rapid and economical manner using a combination of high-throughput methods.

This integration of high-throughput methods together provide a platform that is particularly suited for the rapid and reliable identification and detection of polymorphisms in highly complex nucleic acid samples wherein conventional identification and mapping of polymorphisms would be laborious and time-consuming.

One of the things the present inventors have found is a solution for the identification of polymorphisms, preferably Single Nucleotide Polymorphisms, but likewise for (micro) satellites and/or indels, in particular in large genomes. The method is unique in its applicability to large and small genomes alike, but provides particular advantages for large genomes, in particular polyploidal species.

To identify SNPs (and subsequently detect the identified SNPs) there are several possibilities available in the art. In a first option the whole genome can be sequenced, and this can be done so for several individuals. This is mostly a theoretical exercise as this is cumbersome and expensive and, despite the rapid development of technology simply not feasible to do for every organism, especially the ones with larger genomes. Second option is to use available (fragmented) sequence information, such as EST libraries. This allows the generation of PCR primers, resequencing and comparison between individuals. Again, this requires initial sequence information that is not available or only in a limited amount. Furthermore separate PCR-assays have to be developed for each region which adds enormously to costs and development time.

The third option is to limit one self to part of the genome for each individual. The difficulty resides that the provided part of the genome must be the same for different individuals in order to provide comparable result for successful SNP identification. The present inventors now have solved this dilemma by integration of highly reproducible methods for selecting part of genome with high throughput sequencing for the identification of polymorphisms integrated with sample preparation and high throughput identification platforms. The present invention accelerates the process of polymorphism discovery and uses the same elements in the subsequent process for the exploitation of the discovered polymorphisms to allow for effective and reliable high throughput genotyping.

Further envisaged applications of the method of the present invention include screening enriched microsatellite libraries, performing transcript profiling cDNA-AFLP (digital Northern), sequencing of complex genomes, EST library sequencing (on whole cDNA or cDNA-AFLP), microRNA discovery (sequencing of small insert libraries), Bacterial Artificial Chromosome (BAC)(contig) sequencing, Bulked Segregant analysis approach AFLP/cDNA-AFLP, routine detection of AFLP fragments, e.g. for marker-assisted backcrosses (MABC), etcetera.

DEFINITIONS

In the following description and examples a number of terms are used. In order to provide a clear and consistent understanding of the specification and claims, including the scope to be given such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

Polymorphism: polymorphism refers to the presence of two or more variants of a nucleotide sequence in a population. A polymorphism may comprise one or more base changes, an insertion, a repeat, or a deletion. A polymorphism includes e.g. a simple sequence repeat (SSR) and a single nucleotide polymorphism (SNP), which is a variation, occurring when a single nucleotide: adenine (A), thymine (T), cytosine (C) or guanine (G)—is altered. A variation must generally occur in at least 1% of the population to be considered a SNP. SNPs make up e.g. 90% of all human genetic variations, and occur every 100 to 300 bases along the human genome. Two of every three SNPs substitute Cytosine (C) with Thymine (T). Variations in the DNA sequences of e.g. humans or plants can affect how they handle diseases, bacteria, viruses, chemicals, drugs, etc.

Nucleic acid: a nucleic acid according to the present invention may include any polymer or oligomer of pyrimidine and purine bases, preferably cytosine, thymine, and uracil, and adenine and guanine, respectively (See Albert L. Lehninger, *Principles of Biochemistry*, at 793-800 (Worth Pub. 1982) which is herein incorporated by reference in its entirety for all purposes). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogenous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

Complexity reduction: the term complexity reduction is used to denote a method wherein the complexity of a nucleic acid sample, such as genomic DNA, is reduced by the generation of a subset of the sample. This subset can be representative for the whole (i.e. complex) sample and is preferably a reproducible subset. Reproducible means in this context that when the same sample is reduced in complexity using the same method, the same, or at least comparable, subset is obtained. The method used for complexity reduction may be any method for complexity reduction known in the art. Examples of methods for complexity reduction include for example AFLP® (Keygene N. V., the Netherlands; see e.g. EP 0 534 858), the methods described by Dong (see e.g. WO 03/012118, WO 00/24939), indexed linking (Unrau et al., vide infra), etc. The complexity reduction methods used in the present invention have in common that they are reproducible. Reproducible in the sense that when the same sample is reduced in complexity in the same manner, the same subset of the sample is obtained, as opposed to more random complexity reduction such as microdissection or the use of mRNA (cDNA) which represents a portion of the genome transcribed in a selected tissue and for its reproducibilty is depending on the selection of tissue, time of isolation etc.

Tagging: the term tagging refers to the addition of a tag to a nucleic acid sample in order to be able to distinguish it from a second or further nucleic acid sample. Tagging can e.g. be performed by the addition of a sequence identifier during complexity reduction or by any other means known in the art. Such sequence identifier can e.g. be a unique base sequence of varying but defined length uniquely used for identifying a specific nucleic acid sample. Typical examples thereof are for instance ZIP sequences. Using such tag, the origin of a sample can be determined upon further processing. In case of combining processed products originating from different nucleic acid samples, the different nucleic acid samples should be identified using different tags.

Tagged library: the term tagged library refers to a library of tagged nucleic acid.

Sequencing: The term sequencing refers to determining the order of nucleotides (base sequences) in a nucleic acid sample, e.g. DNA or RNA.

Aligning and alignment: With the term "aligning" and "alignment" is meant the comparison of two or more nucleotide sequence based on the presence of short or long stretches of identical or similar nucleotides. Several methods for alignment of nucleotide sequences are known in the art, as will be further explained below.

Detection probes: The term "detection probes" is used to denote probes designed for detecting a specific nucleotide sequence, in particular sequences containing one or more polymorphisms.

High-throughput screening: High-throughput screening, often abbreviated as HTS, is a method for scientific experimentation especially relevant to the fields of biology and chemistry. Through a combination of modern robotics and other specialised laboratory hardware, it allows a researcher to effectively screen large amounts of samples simultaneously.

Test sample nucleic acid: The term "test sample nucleic acid" is used to indicate a nucleic acid sample that is investigated for polymorphisms using the method of the present invention.

Restriction endonuclease: a restriction endonuclease or restriction enzyme is an enzyme that recognizes a specific nucleotide sequence (target site) in a double-stranded DNA molecule, and will cleave both strands of the DNA molecule at every target site.

Restriction fragments: the DNA molecules produced by digestion with a restriction endonuclease are referred to as restriction fragments. Any given genome (or nucleic acid, regardless of its origin) will be digested by a particular restriction endonuclease into a discrete set of restriction fragments. The DNA fragments that result from restriction endonuclease cleavage can be further used in a variety of techniques and can for instance be detected by gel electrophoresis.

Gel electrophoresis: in order to detect restriction fragments, an analytical method for fractionating double-stranded DNA molecules on the basis of size can be required. The most commonly used technique for achieving such fractionation is (capillary) gel electrophoresis. The rate at which DNA fragments move in such gels depends on their molecular weight; thus, the distances travelled decrease as the fragment lengths increase. The DNA fragments fractionated by gel electrophoresis can be visualized directly by a staining procedure e.g. silver staining or staining using ethidium bromide, if the number of fragments included in the pattern is sufficiently small. Alternatively further treatment of the DNA fragments may incorporate detectable labels in the fragments, such as fluorophores or radioactive labels.

Ligation: the enzymatic reaction catalyzed by a ligase enzyme in which two double-stranded DNA molecules are covalently joined together is referred to as ligation. In general, both DNA strands are covalently joined together, but it is also possible to prevent the ligation of one of the two strands through chemical or enzymatic modification of one of the ends of the strands. In that case the covalent joining will occur in only one of the two DNA strands.

Synthetic oligonucleotide: single-stranded DNA molecules having preferably from about 10 to about 50 bases, which can be synthesized chemically are referred to as synthetic oligonucleotides. In general, these synthetic DNA molecules are designed to have a unique or desired nucleotide sequence, although it is possible to synthesize families of molecules having related sequences and which have different nucleotide compositions at specific positions within the nucleotide sequence. The term synthetic oligonucleotide will be used to refer to DNA molecules having a designed or desired nucleotide sequence.

Adaptors: short double-stranded DNA molecules with a limited number of base pairs, e.g. about 10 to about 30 base pairs in length, which are designed such that they can be ligated to the ends of restriction fragments. Adaptors are generally composed of two synthetic oligonucleotides which have nucleotide sequences which are partially complementary to each other. When mixing the two synthetic oligonucleotides in solution under appropriate conditions, they will anneal to each other forming a double-stranded structure. After annealing, one end of the adaptor molecule is designed such that it is compatible with the end of a restriction fragment and can be ligated thereto; the other end of the adaptor can be designed so that it cannot be ligated, but this need not be the case (double ligated adaptors).

Adaptor-ligated restriction fragments: restriction fragments that have been capped by adaptors.

Primers: in general, the term primers refers to a DNA strand which can prime the synthesis of DNA. DNA polymerase cannot synthesize DNA de novo without primers: it can only extend an existing DNA strand in a reaction in which the complementary strand is used as a template to direct the order of nucleotides to be assembled. We will refer to the synthetic oligonucleotide molecules which are used in a polymerase chain reaction (PCR) as primers.

DNA amplification: the term DNA amplification will be typically used to denote the in vitro synthesis of double-stranded DNA molecules using PCR. It is noted that other amplification methods exist and they may be used in the present invention without departing from the gist.

DETAILED DESCRIPTION OF THE INVENTION

The present invention provides for a method for identifying one or more polymorphisms, said method comprising the steps of:
 a) providing a first nucleic acid sample of interest;
 b) performing a complexity reduction on the first nucleic acid sample of interest to provide a first library of the first nucleic acid sample;
 c) consecutively or simultaneously performing steps a) and b) with a second or further nucleic acid sample of interest to obtain a second or further library of the second or further nucleic acid sample of interest;
 d) sequencing of at least a portion of the first library and the second or further library;
 e) aligning the sequences obtained in step d);
 f) determining one or more polymorphisms between the first nucleic acid sample and second or further nucleic acid sample in the alignment of step e);
 g) using the one or more polymorphisms determined in step f) to design one or more detection probes;
 h) providing a test sample nucleic acid of interest;
 i) performing the complexity reduction of step b) on the test sample nucleic acid of interest to provide a test library of the test sample nucleic acid;
 j) subjecting the test library to high-throughput screening to identify the presence, absence or amount of the polymorphisms determined in step f) using the one or more detection probes designed in step g).

In step a), a first nucleic acid sample of interest is provided. Said first nucleic acid sample of interest is preferably a complex nucleic acid sample such as total genomic DNA or a cDNA library. It is preferred that the complex nucleic acid sample is total genomic DNA.

In step b), a complexity reduction is performed on the first nucleic acid sample of interest to provide a first library of the first nucleic acid sample.

In one embodiment of the invention, the step of complexity reduction of the nucleic acid sample comprises enzymatically cutting the nucleic acid sample in restriction fragments, separating the restriction fragments and selecting a particular pool of restriction fragments. Optionally, the selected fragments are then ligated to adaptor sequences containing PCR primer templates/binding sequences.

In one embodiment of complexity reduction, a type IIs endonuclease is used to digest the nucleic acid sample and the restriction fragments are selectively ligated to adaptor sequences. The adaptor sequences can contain various nucleotides in the overhang that is to be ligated and only the adaptor with the matching set of nucleotides in the overhang is ligated to the fragment and subsequently amplified. This technology is depicted in the art as 'indexing linkers'. Examples of this principle can be found inter alia in Unrau P. and Deugau K. V. (1994) Gene 145:163-169.

In another embodiment, the method of complexity reduction utilizes two restriction endonucleases having different target sites and frequencies and two different adaptor sequences.

In another embodiment of the invention, the step of complexity reduction comprises performing an Arbitrarily Primed PCR upon the sample.

In yet another embodiment of the invention, the step of complexity reduction comprises removing repeated sequences by denaturing and reannealing the DNA and then removing double-stranded duplexes.

In another embodiment of the invention, the step of complexity reduction comprises hybridizing the nucleic acid sample to a magnetic bead which is bound to an oligonucleotide probe containing a desired sequence. This embodiment may further comprise exposing the hybridized sample to a single strand DNA nuclease to remove the single-stranded DNA, ligating an adaptor sequence containing a Class IIs restriction enzyme to release the magnetic bead. This embodiment may or may not comprise amplification of the isolated DNA sequence. Furthermore, the adaptor sequence may or may not be used as a template for the PCR oligonucleotide primer. In this embodiment, the adaptor sequence may or may not contain a sequence identifier or tag.

In another embodiment, the method of complexity reduction comprises exposing the DNA sample to a mismatch binding protein and digesting the sample with a 3' to 5' exonuclease and then a single strand nuclease. This embodiment may or may not include the use of a magnetic bead attached to the mismatch binding protein.

In another embodiment of the present invention, complexity reduction comprises the CHIP method as described herein elsewhere or the design of PCR primers directed against conserved motifs such as SSRs, NBS regions (nucleotide biding regions), promoter/enhancer sequences, telomer consensus sequences, MADS box genes, ATP-ase gene families and other gene families.

In step c), steps a) and b) are consecutively or simultaneously performed with a second or further nucleic acid sample of interest to obtain a second or further library of the second or further nucleic acid sample of interest. Said second or further nucleic acid sample of interest is preferably also a complex nucleic acid sample such as total genomic DNA. It is preferred that the complex nucleic acid sample is total genomic DNA. It is also preferred that said second or further nucleic acid sample is related to the first nucleic acid sample. The first nucleic acid sample and the second or further nucleic acid may for example be different lines of a plant, such as different pepper lines, or different varieties. Steps a) en b) may be performed for merely a second nucleic acid sample of interest, but may also additionally be performed for a third, fourth, fifth, etc. nucleic acid sample of interest.

It is to be noted that the method according to the present invention will be most useful when complexity reduction is performed using the same method and under substantially the same, preferably identical, conditions for the first nucleic acid sample and the second or further nucleic acid sample. Under such conditions, similar (comparable) fractions of the (complex) nucleic acid samples will be obtained.

In step d), at least a portion of the first library and of the second or further library is sequenced. It is preferred that the amount of overlap of sequenced fragments from the first library and second or further library is at least 50%, more preferably at least 60%, yet more preferably at least 70%, even more preferably at least 80%, yet more preferably at least 90%, and most preferably at least 95%.

The sequencing may in principle be conducted by any means known in the art, such as the dideoxy chain termination method. It is however preferred that the sequencing is performed using high-throughput sequencing methods, such as the methods disclosed in WO 03/004690, WO 03/054142, WO 2004/069849, WO 2004/070005, WO 2004/070007, and WO 2005/003375 (all in the name of 454 Corporation), by Seo et al. (2004) Proc. Natl. Acad. Sci. USA 101:5488-93, and technologies of Helios, Solexa, US Genomics, etcetera, which are herein incorporated by reference. It is most preferred that sequencing is performed using the apparatus and/or method disclosed in WO 03/004690, WO 03/054142, WO 2004/069849, WO 2004/070005, WO 2004/070007, and WO 2005/003375 (all in the name of 454 Corporation), which are herein incorporated by reference. The technology described allows sequencing of 40 million bases in a single run and is 100 times faster and cheaper than competing technology. The sequencing technology roughly consists of 4 steps: 1) fragmentation of DNA and ligation of specific adaptor to a library of single-stranded DNA (ssDNA); 2) annealing of ssDNA to beads and emulsification of the beads in water-in-oil microreactors; 3) deposition of DNA carrying beads in a PicoTiter-Plate®; and 4) simultaneous sequencing in 100,000 wells by generation of a pyrophosphate light signal. The method will be explained in more detail below.

In step e), the sequences obtained in step d) are aligned to provide an alignment. Methods of alignment of sequences for comparison purposes are well known in the art. Various programs and alignment algorithms are described in: Smith and Waterman (1981) Adv. Appl. Math. 2:482; Needleman and Wunsch (1970) J. Mol. Biol. 48:443; Pearson and Lipman (1988) Proc. Natl. Acad. Sci. USA 85:2444; Higgins and Sharp (1988) Gene 73:237-244; Higgins and Sharp (1989) CABIOS 5:151-153; Corpet et al. (1988) Nucl. Acids Res. 16:10881-90; Huang et al. (1992) Computer Appl. in the Biosci. 8:155-65; and Pearson et al. (1994) Meth. Mol. Biol. 24:307-31, which are herein incorporated by reference. Altschul et al. (1994) Nature Genet. 6:119-29 (herein incorporated by reference) present a detailed consideration of sequence alignment methods and homology calculations.

The NCBI Basic Local Alignment Search Tool (BLAST) (Altschul et al., 1990) is available from several sources, including the National Center for Biological Information (NCBI, Bethesda, Md.) and on the Internet, for use in connection with the sequence analysis programs blastp, blastn, blastx, tblastn and tblastx. A further application can be in microsatellite mining (see Varshney et al. (2005) Trends in Biotechn. 23(1):48-55.

Typically, the alignment is performed on the sequence data that have been trimmed for the adaptors/primer and/or identifiers, i.e. using only the sequence data from the fragments that originate from the nucleic acid sample. Typically, the sequence data obtained are used for identifying the origin of the fragment (i.e. from which sample), the sequences derived from the adaptor and/or identifier are removed from the data and alignment is performed on this trimmed set.

In step f), one or more polymorphisms are determined between the first nucleic acid sample and second or further nucleic acid sample in the alignment. The alignment can be made such that the sequences derived from the first nucleic acid sample and the second or further nucleic acid sample can be compared. Differences can then be identified reflecting polymorphisms.

In step g) the one or more polymorphisms determined in step g) are used to design detection probes, for example for detection by hybridization on DNA chips or a beads-based detection platform. The detection probes are designed such that a polymorphism is reflected therein. In case of single nucleotide polymorphisms (SNPs) the detection probes typically contain the variant SNP alleles at the central position such as to maximize allele discrimination. Such probes can advantageously be used to screen test samples having a certain polymorphism. The probes can be synthesized using any method known in the art. The probes are typically designed such that they are suitable for high throughput screening methods.

In step h), a test sample nucleic acid of interest is provided. The test sample nucleic acid may be any sample, but is preferably another line or variety to be mapped for polymorphisms. Commonly, a collection of test samples representing the germplasm of the organisms studied is used to validate experimentally that the (SN) polymorphism is genuine and detectable and to calculate allele frequencies of the observed alleles. Optionally, samples of a genetic mapping population are included in the validation step in order to determine the genetic map position of the polymorphism too.

In step i), the complexity reduction of step b) is performed on the test sample nucleic acid of interest to provide a test library of the test sample nucleic acid. It is highly preferred that throughout the method according to the present invention the same method for complexity reduction is used using substantially the same, preferably identical, conditions, thus covering a similar fraction of the sample. It is however not required that a tagged test library is obtained, although a tag may be present on the fragments in the test library.

In step j) the test library is subjected to high-throughput screening to identify the presence, absence or amount of the polymorphisms determined in step f) using the detection probes designed in step g). One skilled in the art knows several methods for high-throughput screening using probes. It is preferred that one or more probes designed using the information obtained in step g) are immobilized on an array, such as a DNA chip, and that such array is subsequently contacted with the test library under hybridizing conditions. DNA fragments within the test library complementary to one or more probes on the array will under such conditions hybridize to such probes, and can thus be detected. Other methods of high-throughput screening are also envisaged within the scope of the present invention, such as immobilization of the test library obtained in step j) and contacting of said immobilized test library with the probes designed in step h) under hybridizing conditions.

Another high-throughput sequencing screening technique is provided inter alia by Affymetrix using chip-based detection of SNPs and bead technology provided by Illumina.

In an advantageous embodiment, step b) in the method according to the present invention further comprises the step of tagging of the library to obtain a tagged library, and said method further comprising step c1) of combining the first tagged library and second or further tagged library to obtain a combined library.

It is preferred that the tagging is performed during the complexity reduction step as to reduce the amount of steps required to obtain the first tagged library of the first nucleic acid sample. Such simultaneous tagging can e.g. be achieved by AFLP, using adaptors that comprise a unique (nucleotide) identifier for each sample.

The tagging is intended to distinguish between samples of different origin, e.g. obtained from different plant lines, when the libraries of two or more nucleic acid samples are combined to obtain a combination library. Thus, preferably different tags are used for preparing the tagged libraries of the first nucleic acid sample and the second or further nucleic acid sample. When for example five nucleic acid samples are used, it is intended to obtain five differently tagged libraries, the five different tags denoting the respective original samples.

The tag may be any tag known in the art for distinguishing nucleic acid samples, but is preferably a short identifier sequence. Such identifier sequence can e.g. be a unique base sequence of varying length used to indicate the origin of the library obtained by complexity reduction.

In a preferred embodiment, the tagging of the first library and the second or further library is performed using different tags. As discussed above, it is preferred that each library of a nucleic acid sample is identified by its own tag. The test sample nucleic acid does not need to be tagged.

In a preferred embodiment of the invention, the complexity reduction is performed by means of AFLP® (Keygene N. V., the Netherlands; see e.g. EP 0 534 858 and Vos et al. (1995). AFLP: a new technique for DNA fingerprinting, *Nucleic Acids Research*, vol. 23, no. 21, 4407-4414, which are herein incorporated in their entirety by reference).

AFLP is a method for selective restriction fragment amplification. AFLP does not any prior sequence information and can be performed on any starting DNA. In general, AFLP comprises the steps of:
  (a) digesting a nucleic acid, in particular a DNA or cDNA, with one or more specific restriction endonucleases, to fragment the DNA into a corresponding series of restriction fragments;
  (b) ligating the restriction fragments thus obtained with a double-stranded synthetic oligonucleotide adaptor, one end of which is compatible with one or both of the ends of the restriction fragments, to thereby produce adapter-ligated, preferably tagged, restriction fragments of the starting DNA;
  (c) contacting the adapter-ligated, preferably tagged, restriction fragments under hybridizing conditions with at least one oligonucleotide primer that contains at least one selective nucleotide at its 3'-end;
  (d) amplifying the adapter-ligated, preferably tagged, restriction fragment hybridised with the primers by PCR or a similar technique so as to cause further elongation of the hybridised primers along the restriction fragments of the starting DNA to which the primers hybridised; and
  (e) detecting, identifying or recovering the amplified or elongated DNA fragment thus obtained.

AFLP thus provides a reproducible subset of adaptor-ligated fragments. Other suitable methods for complexity reduction are Chromatine Immuno Precipitation (ChiP). This means that nuclear DNA is isolated, whilst proteins such as transcription factors are linked to the DNA. With ChiP first an antibody is used against the protein, resulting in Ab-protein-DNA complex. By purifying this complex and precipitating it, DNA to which this protein binds is selected. Subsequently, the DNA can be used for library construction and sequencing. I.e., this is a method to perform a complexity reduction in a non-random fashion directed to specific functional areas; in the present example specific transcription factors.

One useful variant of the AFLP technology uses no selective nucleotides (i.c. +0/+0 primers) and is sometimes called linker PCR. This also provides for a very suitable complexity reduction.

For a further description of AFLP, its advantages, its embodiments, as well as the techniques, enzymes, adaptors, primers and further compounds and tools used therein, reference is made to U.S. Pat. No. 6,045,994, EP-B-0 534 858, EP 976835 and EP 974672, WO01/88189 and Vos et al. Nucleic Acids Research, 1995, 23, 4407-4414, which are hereby incorporated in their entirety.

Thus, in a preferred embodiment of the method of the present invention, the complexity reduction is performed by
  digesting the nucleic acid sample with at least one restriction endonuclease to fragment it into restriction fragments;
  ligating the restriction fragments obtained with at least one double-stranded synthetic oligonucleotide adaptor having one end compatible with one or both ends of the restriction fragments to produce adapter-ligated restriction fragments;
  contacting said adapter-ligated restriction fragments with one or more oligonucleotide primers under hybridizing conditions; and
  amplifying said adapter-ligated restriction fragments by elongation of the one or more oligonucleotide primers,
  wherein at least one of the one or more oligonucleotide primers include a nucleotide sequence having the same nucleotide sequence as the terminal parts of the strands at the ends of said adapter-ligated restriction fragments, including the nucleotides involved in the formation of the target sequence for said restriction endonuclease and including at least part of the nucleotides present in the adaptors, wherein, optionally, at least one of said primers includes at its 3' end a selected sequence comprising at least one nucleotide located immediately adjacent to the nucleotides involved in the formation of the target sequence for said restriction endonuclease.

AFLP is a highly reproducible method for complexity reduction and is therefore particularly suited for the method according to the present invention.

In a preferred embodiment of the method according to the present invention, the adaptor or the primer comprises a tag. This is particularly the case for the actual identification of the polymorphisms, when it is important to distinguish between sequences derived from separate libraries. Incorporating an oligonucleotide tag in an adaptor or primer is very convenient as no additional steps are required to tag a library.

In another embodiment, the tag is an identifier sequence. As discussed above, such identifier sequence may be of varying length depending on the amount of nucleic acid samples to be compared. A length of about 4 bases ($4^4$=256 different tag sequences possible) is sufficient to distinguish between the origin of a limited number of samples (up to 256), although it is preferred that the tag sequences differ by more than one base between the samples to be distinguished. As needed, the length of the tag sequences can be adjusted accordingly.

In an embodiment, the sequencing is performed on a solid support such as a bead (see e.g. WO 03/004690, WO 03/054142, WO 2004/069849, WO 2004/070005, WO 2004/070007, and WO 2005/003375 (all in the name of 454 Corporation), which are herein incorporated by reference). Such sequencing method is particularly suitable for cheap and efficient sequencing of many samples simultaneously.

In a preferred embodiment, the sequencing comprises the steps of:
annealing adapter-ligated fragments to beads, each bead being annealed with a single adapter-ligated fragment;
emulsifying the beads in water-in-oil microreactors, each water-in-oil microreactor comprising a single bead;
loading the beads in wells, each well comprising a single bead; and
generating a pyrophosphate signal.

In the first step, sequencing adaptors are ligated to fragments within the combination library. Said sequencing adaptor includes at least a "key" region for annealing to a bead, a sequencing primer region and a PCR primer region. Thus, adapter-ligated fragments are obtained.

In a further step, adapter-ligated fragments are annealed to beads, each bead annealing with a single adapter-ligated fragment. To the pool of adapter-ligated fragments, beads are added in excess as to ensure annealing of one single adapter-ligated fragment per bead for the majority of the beads (Poisson distribution).

In a next step, the beads are emulsified in water-in-oil microreactors, each water-in-oil microreactor comprising a single bead. PCR reagents are present in the water-in-oil microreactors allowing a PCR reaction to take place within the microreactors. Subsequently, the microreactors are broken, and the beads comprising DNA (DNA positive beads) are enriched.

In a following step, the beads are loaded in wells, each well comprising a single bead. The wells are preferably part of a PicoTiter™ Plate allowing for simultaneous sequencing of a large amount of fragments.

After addition of enzyme-carrying beads, the sequence of the fragments is determined using pyrosequencing. In successive steps, the picotiterplate and the beads as well as the enzyme beads therein are subjected to different deoxyribonucleotides in the presence of conventional sequencing reagents, and upon incorporation of a deoxyribonucleotide a light signal is generated which is recorded. Incorporation of the correct nucleotide will generate a pyrosequencing signal which can be detected.

Pyrosequencing itself is known in the art and described inter alia on www.biotagebio.com; www.pyrosequencing.com/tab technology The technology is further applied in e.g. WO 03/004690, WO 03/054142, WO 2004/069849, WO 2004/070005, WO 2004/070007, and WO 2005/003375 (all in the name of 454 Corporation), which are herein incorporated by reference.

The high-throughput screening of step k) is preferably performed by immobilization of the probes designed in step h) onto an array, followed by contacting of the array comprising the probes with a test library under hybridizing conditions. Preferably, the contacting step is performed under stringent hybridizing conditions (see Kennedy et al. (2003) Nat. Biotech.; published online 7 Sep. 2003: 1-5). One skilled in the art is aware of suitable methods for immobilization of probes onto an array and of methods of contacting under hybridizing conditions. Typical technology that is suitable for this purpose is reviewed in Kennedy et al. (2003) Nat. Biotech.; published online 7 Sep. 2003: 1-5.

One particular advantageous application is found in the breeding of polyploidal crops. By sequencing polyploidal crops with a high coverage, identifying SNPs and the various alleles and developing probes for allele-specific amplification significant progress can be made the breeding of polyploidal crops.

As part of the invention, it has been found that the combination of generating random selected subsets using selective amplification for a plurality of samples and high throughput sequencing technology presents certain complex problems that had to be solved for the further improvement of the herein described method for the efficient and high throughput identification of polymorphisms. More in detail, it has been found that when multiple (i.e. the first and the second or further) samples are combined in a pool after performing a complexity reduction, a problem occurs that many fragments appear to be derived from two samples, or, put differently, many fragments were identified that could not be allocated uniquely to one sample and thus could not be used in the process of identifying polymorphisms. This lead to a reduced reliability of the method and to less polymorphisms (SNPs, indels, SSRs) that could be adequately identified.

After careful and detailed analysis of the entire nucleotide sequence of the fragments that could not be allocated, it was found that those fragments contained two different tag-comprising adaptors and were probably formed between the generation of the complexity reduced samples and the ligation of the sequencing adaptors. The phenomenon is depicted as 'mixed tagging'. The phenomenon depicted as 'mixed tagging', as used herein, thus refers to fragments that contain a tag relating the fragment to one sample on side, whereas the opposite side of the fragment contains a tag relating the fragment to another sample. Thus one fragment appears to be derived from two samples (quod non). This leads to erroneous identification of polymorphisms and is hence undesirable.

It has been theorised that the formation of heteroduplex fragments between two samples lies afoot to this anomaly.

The solution to this problem has been found in a redesigning of the strategy for the conversion of samples of which the complexity is reduced to bead-annealed fragments that can be amplified prior to high throughput sequencing. In this embodiment, each sample is subjected to complexity reduction and optional purification. After that, each sample is rendered blunt (end-polishing) followed by ligation of the sequencing adapter that is capable of annealing to the bead. The sequencing adapter-ligated fragments of the samples are then combined and ligated to the beads for emulsion polymerisation and subsequent high-throughput sequencing.

As a further part of this invention, it was found that the formation of concatamers hampered the proper identification of polymorphisms. Concatamers have been identified as fragments that are formed after complexity reduction products have been 'blunted' or 'polished', for instance by T4 DNA polymerase, and instead of ligating to the adapters that allow annealing to the beads, ligate to each other, hereby creating concatamers, i.e. a concatamer is the result of the dimerisation of blunted fragments.

The solution to his problem was found in the use of certain specifically modified adapters. The amplified fragments obtained from the complexity reduction typically contain a 3'-A overhang due to the characteristics of certain preferred polymerases that do not have 3'-5' exonuclease proof-reading activity. The presence of such a 3'-A overhang is also the reason why fragments are blunted prior to adapter ligation. By providing an adapter that can anneal to a bead wherein the adapter contains a 3'-T overhang, it was found that both the problem of the 'mixed tags' and of the concatamers can be solved in one step. A further advantage of using these modified adapters is that the conventional 'blunting' step and the subsequent phosporylation step can be omitted.

Thus, in a further preferred embodiment, after the complexity reduction step of each sample, a step is performed on the amplified adapter-ligated restriction fragments obtained from the complexity reduction step, whereby to these fragments sequencing adapters are ligated, which sequencing adapters contain a 3'-T overhang and are capable of annealing to the beads.

It has further been found that, when the primers used in the complexity reduction step are phosporylated, the end-polishing (blunting) step and intermediate phosporylation prior to ligation can be avoided.

Thus, in a highly preferred embodiment of the invention, the invention relates to a method for identifying one or more polymorphisms, said method comprising the steps of:
a) providing a plurality of nucleic acid samples of interest;
b) performing a complexity reduction on each of the samples to provide a plurality of libraries of the nucleic acid samples, wherein the complexity reduction is performed by
  digesting each nucleic acid sample with at least one restriction endonuclease to fragment it into restriction fragments;
  ligating the restriction fragments obtained with at least one double-stranded, synthetic oligonucleotide adaptor having one end compatible with one or both ends of the restriction fragments to produce adapter-ligated restriction fragments;
  contacting said adapter-ligated restriction fragments with one or more phosporylated oligonucleotide primers under hybridising conditions; and
  amplifying said adapter-ligated restriction fragments by elongation of the one or more oligonucleotide primers, wherein at least one of the one or more oligonucleotide primers include a nucleotide sequence having the same nucleotide sequence as the terminal parts of the strands at the ends of said adapter-ligated restriction fragments, including the nucleotides involved in the formation of the target sequence for said restriction endonuclease and including at least part of the nucleotides present in the adaptors, wherein, optionally, at least one of said primers includes at its 3' end a selected sequence comprising at least one nucleotide located immediately adjacent to the nucleotides involved in the formation of the target sequence for said restriction endonuclease and wherein the adaptor and/or the primer contain a tag;
c) combining said libraries to a combined library;
d) ligating sequencing adapters capable of annealing to beads to the amplified adapter-capped fragments in the combined library, using an sequencing adapter carrying a 3'-T overhang and subjecting the bead-annealed fragments to emulsion polymerisation;
e) sequencing of at least a portion of the combined library;
f) aligning the sequences from each sample obtained in step e);
g) determining one or more polymorphisms between the plurality of nucleic acid samples in the alignment of step f);
h) using the one or more polymorphisms determined in step g) to design detection probes;
i) providing a test sample nucleic acid of interest;
j) performing the complexity reduction of step b) on the test sample nucleic acid of interest to provide a test library of the test sample nucleic acid;
k) subjecting the test library to high-throughput screening to identify the presence, absence or amount of the polymorphisms determined in step g) using the detection probes designed in step h).

BRIEF DESCRIPTION OF THE DRAWINGS

FIG. 1A shows the primer sequences for preamplification of PSP-11 and PI20234. FIG. 1A also shows a fragment according to the present invention annealed onto a bead ('454 bead') and the sequence of primer used for pre-amplification of the two pepper lines. 'DNA fragment' denotes the fragment obtained after digestion with a restriction endonuclease, 'keygene adaptor' denotes an adaptor providing an annealing site for the (phosphorylated) oligonucleotide primers used to generate a library, 'KRS' denotes an identifier sequence (tag), '454 SEQ. Adaptor' denotes a sequencing adaptor, and '454 PCR adaptor' denotes an adaptor to allow for emulsion amplification of the DNA fragment. The PCR adaptor allows for annealing to the bead and for amplification and may contain a 3'-T overhang.

FIG. 1B shows a schematic primer used in the complexity reduction step. Such a primer generally comprises a recognition site region indicated as (2), a constant region that may include a tag section indicated as (1) and one or more selective nucleotides in a selective region indicated as (3) at the 3'-end thereof).

FIGS. 2A and 2B show DNA concentration estimation using 2% agarose gel-electrophoresis. S1 denotes PSP11; S2 denote PI201234. 50, 100, 250 and 500 ng denotes respectively 50 ng, 100 ng, 250 ng and 500 ng to estimate DNA amounts of S1 and S2. FIGS. 2C and 2D show DNA concentration determination using NanoDrop® spectrophotometry.

FIGS. 3A and 3B show the results of intermediate quality assessments of example 3. FIG. 3C shows DNA concentrations of each sample noted using NanoDrop® spectrophotometry.

FIG. 4A shows flow charts of the sequence data processing pipeline, i.e. the steps taken from the generation of the sequencing data to the identification of putative SNPs, SSRs and indels, via steps of the removal of known sequence information in Trimming & Tagging resulting in trimmed sequence data which are clustered and assembled to yield contigs and singletons (fragments that cannot be assembled in a contig) after which putative polymorphisms can be identified and assessed. FIG. 4B further elaborates on the process of polymorphisms mining.

FIGS. 5A, 5B and 5C address the problem of mixed tags and provides in panel 1 an example of a mixed tag, carrying tags associated with sample 1 (MS1) and sample 2 (MS2). Panel 2 provides a schematic explanation of the phenomenon. AFLP Restriction fragments derived from sample 1 (S1) and from sample 2 (S2) are ligated with adaptors ("Keygene adaptor") on both sides carrying sample specific tags S1 and S2. After amplification and sequencing, e Expected fragments are those with S1-S1 tags and S2-S2 tags. What additionally and unexpectedly is observed are also fragments that carry tags S1-S2 or S2-S1. Panel 3 explains the hypothesized cause of the generation of mixed tags whereby heteroduplex products are formed from fragments from samples 1 and 2. The heteroduplexes are subsequently, due to the 3'-5' exonuclease activity of T4 DNA polymerase or Klenow, rendered free from the 3'-protruding ends. During polymerization, the gaps are filled with nucleotides and the incorrect tag is introduced. This works for heteroduplexes of about the same length (top panel) but also for heteroduplexes of more varying length. Panel 4 provides on the right the conventional protocol leading to the formation of mixed tags and on the right the modified protocol.

FIGS. 6A, 6B and 6C address the problem of concatamer formation, whereby in panel 1 a typical example of a concatamer is given, whereby the various adapter and tag sections are underlined and with their origin (i.e. MS1, MS2, ES1 and ES2 corresponding respectively to a MseI restriction site-adapter from sample 1, MseI restriction site-adapter from sample 2, EcoRI restriction site-adapter from sample 1, EcoRI restriction site-adapter from sample 2). Panel 2 demonstrates the expected fragments carrying S1-S1 tags and S2-S2 tags and the observed but unexpected S1-S1-S2-S2, being a concatamer of a fragments from sample 1 and from sample 2. Panel 3 solution to avoid the generation of concatamers as well as mixed tags by introducing an overhang in the AFLP adaptors, modified sequencing adaptors and omission of the end-polishing step when ligating sequencing adaptors. No concatamer formation is found because the ALP fragments can not ligate to each other and no mixed fragments occur as the end-polishing step is omitted. Panel 4 provides the modified protocol using modified adaptors to avoid concatamer formation as well as mixed tags.

FIG. 7. Multiple alignment "10037_CL989contig2" of pepper AFLP fragment sequences, containing a putative single nucleotide polymorphism (SNP). Note that the SNP (indicated by an the black arrow) is defined by an A allele present in both reads of sample 1 (PSP11), denoted by the presence of the MS1 tag in the name of the top two reads, and a G allele present in sample 2 (PI201234), denoted by the presence of the MS2 tag in the name of the bottom two reads. Read names are shown on the left. The consensus sequence of this multiple alignment is (5'-3'): TAACACGACTTTGAACAAACCCAAACTCCCCCAATCGATTTCAAACCTAGAACA[A/G]TGTTGGTTTTGGTGCTAACTTCAACCCCACTACTGTTTTGCTCTATTTTTG (SEQ ID NO: 47). FIG. 7 discloses full-length sequences as SEQ ID NOS 64-68, respectively, in order of appearance.

EXAMPLES

Example 1

Figure 5C:
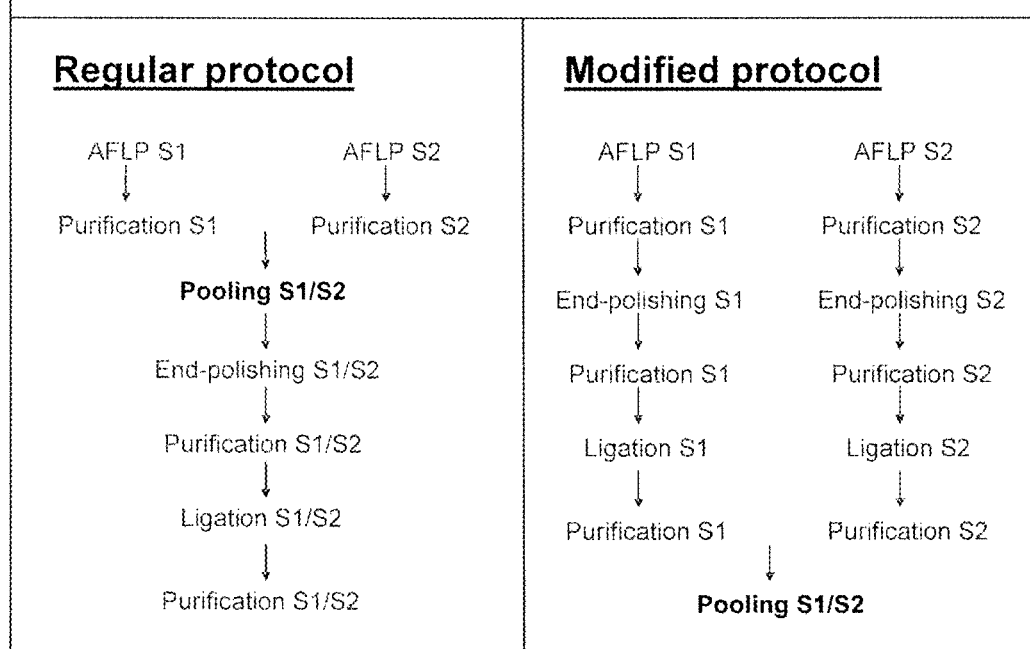

EcoRI/MseI restriction ligation mixture (1) was generated from genomic DNA of the pepper lines PSP-11 and PI20234. The restriction ligation mixture was 10 times diluted and 5 microliter of each sample was pre-amplified (2) with EcoRI+1(A) and MseI+1(C) primers (set I). After amplification the quality of the pre-amplification product of the two pepper samples was checked on a 1% agarose gel. The preamplification products were 20 times diluted, followed by a KRSEcoRI+1(A) and KRSMseI+2(CA) AFLP pre-amplification. The KRS (identifier)sections are underlined and the selective nucleotides are in bold at the 3'-end in the primersequence SEQ ID NO: 1-4 below. After amplification the quality of the pre-amplification product of the two pepper samples was checked on a 1% agarose gel and by an EcoRI+3(A) and MseI+3(C) (3) AFLP fingerprint (4). The pre-amplification products of the two pepper lines were separately purified on a QiagenPCR column (5). The concentration of the samples was measured on the NanoDrop® spectrophotometry. A total of 5006.4 ng PSP-11 and 5006.4 ng PI20234 was mixed and sequenced.

Primer Set I Used for Preamplification of PSP-11

```
E01LKRS1
                                        [SEQ ID NO: 1]
5'-CGTCAGACTGCGTACCAATTCA-3'

M15KKRS1
                                        [SEQ ID NO: 2]
5'-TGGTGATGAGTCCTGAGTAACA-3'
```

Primer Set II Used for Preamplification of PI20234

```
E01LKRS2
                                        [SEQ ID NO: 3]
5'-CAAGAGACTGCGTACCAATTCA-3'

M15KKRS2
                                        [SEQ ID NO: 4]
5'-AGCCGATGAGTCCTGAGTAACA-3'
```

(1) EcoRI/MseI Restriction Ligation Mixture
Restriction Mix (40 ul/Sample)

| DNA | 6 μl (±300 ng) |
|---|---|
| ECoRI (5 U) | 0.1 μl |
| MseI(2 U) | 0.05 μl |
| 5xRL | 8 μl |
| MQ | 25.85 μl |
| Totaal | 40 μl |

Incubation during 1 h. at 37° C.
Addition of:
Ligation Mix (10 μl/Sample)

| 10 mM ATP | 1 μl |
|---|---|
| T4 DNA ligase | 1 μl |

-continued

| ECoRI adapt. (5 pmol/µl) | 1 µl |
| MseI adapt.. (50 pmol/µl) | 1 µl |
| 5xRL | 2 µl |
| MQ | 4 µl |
| Totaal | 10 µl |

Incubation during 3 h. at 37° C.

```
                                              [SEQ ID NO: 5]
91M35/91M36: *-CTCGTAGACTGCGTACC :91M35

[SEQ ID NO: 6]
±bio CATCTGACGCATGGTTAA :91M36
```

MseI-Adaptor

```
                                              [SEQ ID NO: 7]
92A18/92A19: 5-GACGATGAGTCCTGAG-3 :92A18

[SEQ ID NO: 8]
3-TACTCAGGACTCAT-5 :92A19
```

(2) Pre-Amplification
Preamplification (A/C):

| RL-mix (10x) | 5 µl |
| EcoRI-pr E01L(50 ng/ul) | 0.6 µl |
| MseI-pr M02K(50 ng/ul) | 0.6 µl |
| dNTPs (25 mM) | 0.16 µl |
| Taq.pol. (5 U) | 0.08 µl |
| 10XPCR | 2.0 µl |
| MQ | 11.56 µl |
| Total | 20 µl/reaction |

Pre-Amplification Thermal Profile

Selective pre amplification was done in a reaction volume of 50 µl. The PCR was performed in a PE GeneAmp PCR System 9700 and a 20 cycle profile was started with a 94° C. denaturation step for 30 seconds, followed by an annealing step of 56° C. for 60 seconds and an extension step of 72° C. for 60 seconds.

```
EcoRI + 1(A)¹
                                              [SEQ ID NO: 9]
E01 L 92R11: 5-AGACTGCGTACCAATTCA-3

MseI + 1(C)¹
                                              [SEQ ID NO: 10]
M02k 93E42: 5-GATGAGTCCTGAGTAAC-3
```

Preamplification A/CA:

| PA+1/+1-mix (20x) | 5 µl |
| EcoRI-pr | 1.5 µl |
| MseI-pr. | 1.5 µl |
| dNTPs (25 mM) | 0.4 µl |
| Taq.pol. (5 U) | 0.2 µl |
| 10XPCR | 5 µl |
| MQ | 36.3 µl |
| Total | 50 µl |

Selective pre amplification was done in a reaction volume of 50 µl. The PCR was performed in a PE GeneAmp PCR System 9700 and a 30 cycle profile was started with a 94° C. denaturation step for 30 seconds, followed by an annealing step of 56° C. for 60 seconds and an extension step of 72° C. for 60 seconds.

(3) KRSEcoRI+1(A) and KRSMseI+2(CA)²

```
                                              [SEQ ID NO: 11]
05F212 E01LKRS1 CGTCAGACTGCGTACCAATTCA-3'

[SEQ ID NO: 12]
05F213 E01LKRS2 CAAGAGACTGCGTACCAATTCA-3'

[SEQ ID NO: 13]
05F214 M15KKRS1 TGGTGATGAGTCCTGAGTAACA-3'

[SEQ ID NO: 14]
05F215 M15KKRS2 AGCCGATGAGTCCTGAGTAACA-3'
``` selective nucleotides in bold and tags (KRS) underlined
Sample PSP11: E01LKRS1/M15KKRS1
Sample PI120234: E01LKRS2/M15KKRS2

(4) AFLP Protocol

Selective amplification was done in a reaction volume of 20 µl. The PCR was performed in a PE GeneAmp PCR System 9700. A 13 cycle profile was started with a 94° C. denaturation step for 30 seconds, followed by an annealing step of 65° C. for 30 seconds, with a touchdown phase in witch the annealing temperature was lowered 0.7° C. in each cycle, and an extension step of 72° C. for 60 seconds. This profile was followed by a 23 cycle profile with a 94° C. denaturation step for 30 seconds, followed by an annealing step of 56° C. for 30 seconds and an extension step of 72° C. for 60 seconds.

```
EcoRI + 3(AAC) and MseI + 3(CAG)
                                              [SEQ ID NO: 15]
E32 92S02: 5-GACTGCGTACCAATTCAAC-3

[SEQ ID NO: 16]
M49 92G23: 5-GATGAGTCCTGAGTAACAG-3
```

(5) Qiagen Column

Qiagen purification was performed according to the manufacturer's instruction: QIAquick® Spin Handbook.

Example 2: PEPPER

DNA from the Pepper lines PSP-11 and PI20234 was used to generate AFLP product by use of AFLP Keygene Recognition Site specific primers. (These AFLP primers are essentially the same as conventional AFLP primers, e.g. described in EP 0 534 858, and will generally contain a recognition site region, a constant region and one or more selective nucleotides in a selective region.

From the pepper lines PSP-11 or PI20234 150 ng of DNA was digested with the restriction endonucleases EcoRI (5 U/reaction) and MseI (2 U/reaction) for 1 hour at 37° C. following by inactivation for 10 minutes at 80° C. The obtained restriction fragments were ligated with double-stranded synthetic oligonucleotide adapter, one end of witch is compatible with one or both of the ends of the EcoRI and/or MseI restriction fragments. AFLP preamplification reactions (20 µl/reaction) with +1/+1 AFLP primers were performed on 10 times diluted restriction-ligation mixture. PCR profile: 20*(30 s at 94° C.+60 s at 56° C.+120 s at 72° C.). Additional AFLP reactions (50 µl/reaction) with different +1 EcoRI and +2 MseI AFLP Keygene Recognition Site specific primers (Table below, tags are in bold, selective nucleotides are underlined.) were performed on 20 times diluted +1/+1 EcoRI/MseI AFLP preamplification product.

PCR profile: 30*(30 s at 94° C.+60 s at 56° C.+120 s at 72° C.). The AFLP product was purified by using the QIAquick PCR Purification Kit (QIAGEN) following the QIAquick® Spin Handbook July 2002 page 18 and the concentration was measured with a NanoDrop® ND-1000 Spectrophotometer. A total of 5 µg of +1/+2 PSP-11 AFLP product and 5 µg of +1/+2 PI20234 AFLP product was put together and solved in 23.3 µl TE. Finally a mixture with a concentration of 430 ng/µl +1/+2 AFLP product was obtained.

TABLE

| SEQ ID NO | PCR primer | Primer-3' | Pepper | AFLP reaction |
|---|---|---|---|---|
| [SEQ ID NO: 17] | 05F21 | CGTCAGACTGCGT ACCAATTC<u>A</u> | PSP- | 1 |
| [SEQ ID NO: 18] | 05F21 | TGGTGATGAGTCC TGAGTAAC<u>A</u> | PSP- | 1 |
| [SEQ ID NO: 19] | 05F21 | CAAGAGACTGCGT ACCAATTC<u>A</u> | PI2023 | 2 |
| [SEQ ID NO: 20] | 05F21 | AGCCGATGAGTCC TGAGTAAC<u>A</u> | PI2023 | 2 |

Example 3: Maize

DNA from the Maize lines B73 and M017 was used to generate AFLP product by use of AFLP Keygene Recognition Site specific primers. (These AFLP primers are essentially the same as conventional AFLP primers, e.g. described in EP 0 534 858, and will generally contain a recognition site region, a constant region and one or more selective nucleotides at the 3'-end thereof.).

DNA from the pepper lines B73 or M017 was digested with the restriction endonucleases TaqI (5 U/reaction) for 1 hour at 65° C. and MseI (2 U/reaction) for 1 hour at 37° C. following by inactivation for 10 minutes at 80° C. The obtained restriction fragments were ligated with double-stranded synthetic oligonucleotide adapter, one end of witch is compatible with one or both of the ends of the TaqI and/or MseI restriction fragments. AFLP preamplification reactions (20 µl/reaction) with +1/+1 AFLP primers were performed on 10 times diluted restriction-ligation mixture. PCR profile: 20*(30 s at 94° C.+60 s at 56° C.+120 s at 72° C.). Additional AFLP reactions (50 µl/reaction) with different +2 TaqI and MseI AFLP Keygene Recognition Site primers (Table below, tags are in bold, selective nucleotides are underlined.) were performed on 20 times diluted +1/+1 TaqI/MseI AFLP preamplification product. PCR profile: 30*(30 s at 94° C.+60 s at 56° C.+120 s at 72° C.). The AFLP product was purified by using the QIAquick PCR Purification Kit (QIAGEN) following the QIAquick® Spin Handbook July 2002 page 18 and the concentration was measured with a NanoDrop® ND-1000 Spectrophotometer. A total of 1.25 µg of each different B73 +2/+2 AFLP product and 1.25 µg of each different M017 +2/+2 AFLP product was put together and solved in 30 µl TE. Finally a mixture with a concentration of 333 ng/µl+2/+2 AFLP product was obtained.

TABLE

| SEQ ID | PCR Primer | Primer sequence | Maize | AFLP Reaction |
|---|---|---|---|---|
| [SEQ ID NO: 21] | 05G360 | ACGTGTAGACTGCGTACCG A<u>AA</u> | B73 | 1 |
| [SEQ ID NO: 22] | 05G368 | ACGTGATGAGTCCTGAGTA A<u>CA</u> | B73 | 1 |
| [SEQ ID NO: 23] | 05G362 | CGTAGTAGACTGCGTACCG A<u>AC</u> | B73 | 2 |
| [SEQ ID NO: 24] | 05G370 | CGTAGATGAGTCCTGAGTA A<u>CA</u> | B73 | 2 |
| [SEQ ID NO: 25] | 05G364 | GTACGTAGACTGCGTACCG A<u>AG</u> | B73 | 3 |
| [SEQ ID NO: 26] | 05G372 | GTACGATGAGTCCTGAGTA A<u>CA</u> | B73 | 3 |
| [SEQ ID NO: 27] | 05G366 | TACGGTAGACTGCGTACCG A<u>AT</u> | B73 | 4 |
| [SEQ ID NO: 28] | 05G374 | TACGGATGAGTCCTGAGTA A<u>CA</u> | B73 | 4 |
| [SEQ ID NO: 29] | 05G361 | AGTCGTAGACTGCGTACCG A<u>AA</u> | M017 | 5 |
| [SEQ ID NO: 30] | 05G369 | AGTCGATGAGTCCTGAGTA A<u>CA</u> | M017 | 5 |
| [SEQ ID NO: 31] | 05G363 | CATGGTAGACTGCGTACCG A<u>AC</u> | M017 | 6 |
| [SEQ ID NO: 32] | 05G371 | CATGGATGAGTCCTGAGTA A<u>CA</u> | M017 | 6 |
| [SEQ ID NO: 33] | 05G365 | GAGCGTAGACTGCGTACCG A<u>AG</u> | M017 | 7 |

TABLE-continued

| SEQ ID | PCR Primer | Primer sequence | Maize AFLP | Reaction |
|---|---|---|---|---|
| [SEQ ID NO: 34] | 05G373 | GAGCGATGAGTCCTGAGTA A<u>CA</u> | M017 | 7 |
| [SEQ ID NO: 35] | 05G367 | TGATGTAGACTGCGTACCG A<u>AT</u> | M017 | 8 |
| [SEQ ID NO: 36] | 05G375 | TGATGATGAGTCCTGAGTA A<u>CA</u> | M017 | 8 |

Finally the 4 P1-samples and the 4 P2-samples were pooled and concentrated. A total amount of 25 µl of DNA product and a final concentration of 400 ng/ul (total of 10 µg) was obtained. Intermediate quality assessments are given in FIGS. 3A-3C.

Sequencing by 454

Pepper and maize AFLP fragment samples as prepared as described hereinbefore were processed by 454 Life Sciences as described (Margulies et al., 2005. Genome sequencing in microfabricated high-density picoliter reactors. Nature 437 (7057):376-80. Epub Jul. 31, 2005).

Data Processing

Processing Pipeline:

Input Data raw sequence data were received for each run:

200,000-400,000 reads base calling quality scores

Trimming and Tagging

These sequence data are analyzed for the presence of Keygene Recognition Sites (KRS) at the beginning and end of the read. These KRS sequences consist of both AFLP-adaptor and sample label sequence and are specific for a certain AFLP primer combination on a certain sample. The KRS sequences are identified by BLAST and trimmed and the restriction sites are restored. Reads are marked with a tag for identification of the KRS origin. Trimmed sequences are selected on length (minimum of 33 nt) to participate in further processing.

Clustering and Assembly

A MegaBlast analysis is performed on all size-selected, trimmed reads to obtain clusters of homologous sequences. Consecutively all clusters are assembled with CAP3 to result in assembled contigs. From both steps unique sequence reads are identified that do not match any other reads. These reads are marked as singletons.

The processing pipeline carrying out the steps described herein before is shown in FIG. 4A Polymorphism Mining and Quality Assessment The resulting contigs from the assembly analysis form the basis of polymorphism detection. Each 'mismatch' in the alignment of each cluster is a potential polymorphism. Selection criteria are defined to obtain a quality score:

number of reads per contig frequency of 'alleles' per sample occurrence of homopolymer sequence occurrence of neighbouring polymorphisms SNPs and indels with a quality score above the threshold are identified as putative polymorphisms. For SSR mining we used the MISA (MIcroSAtellite identification) tool. This tool identifies di-, tri-, tetranucleotide and compound SSR motifs with predefined criteria and summarizes occurrences of these SSRs.

The polymorphism mining and quality assignment process is shown in FIG. 4B

Results

The table below summarizes the results of the combined analysis of sequences obtained from 2 454 sequence runs for the combined pepper samples and 2 runs for the combined maize samples.

| | Pepper | Maize |
|---|---|---|
| Total number of reads | 457178 | 492145 |
| Number of trimmed reads | 399623 | 411008 |
| Number singletons | 105253 | 313280 |
| Number of contigs | 31863 | 14588 |
| Number of reads in contigs | 294370 | 97728 |
| Total number of sequences containing SSRs | 611 | 202 |
| Number of different SSR-containing sequences | 104 | 65 |
| Number of different SSR motifs (di, tri, tetra and compound) | 49 | 40 |
| Number SNPs with Q score ≥0.3 * | 1636 | 782 |
| Number of indels * | 4090 | 943 |

* both with selection against neighboring SNPs, at least 12 bp flanking sequence and not occurring in homopolymer sequences larger than 3 nucleotides.

Example 4. Single Nucleotide Polymorphism (SNP) Discovery in Pepper

DNA Isolation

Genomic DNA was isolated from the two parental lines of a pepper recombinant inbred (ML) population and 10 ML progeny. The parental lines are PSP11 and PI201234. Genomic DNA was isolated from leaf material of individual seedlings using a modified CTAB procedure described by Stuart and Via (Stuart, C. N., Jr and Via, L. E. (1993) A rapid CTAB DNA isolation technique useful for RAPD fingerprinting and other PCR applications. *Biotechniques*, 14, 748-750). DNA samples were diluted to a concentration of 100 ng/µl in TE (10 mM Tris-HCl pH 8.0, 1 mM EDTA) and stored at −20° C.

AFLP Template Preparation Using Tagged AFLP Primers

AFLP templates of the pepper parental lines PSP11 and PI201234 were prepared using the restriction endonuclease combination EcoRI/MseI as described by Zabeau & Vos, 1993: Selective restriction fragment amplification; a general method for DNA fingerprinting. EP 0534858-A1, B1; U.S. Pat. No. 6,045,994) and Vos et al (Vos, P., Hogers, R., Bleeker, M., Reijans, M., van de Lee, T., Hornes, M., Frijters, A., Pot, J., Peleman, J., Kuiper, M. et al. (1995) AFLP: a new technique for DNA fingerprinting. *Nucl. Acids Res.*, 21, 4407-4414).

Specifically, restriction of genomic DNA with EcoRI and MseI was carried out as follows:

DNA Restriction

| | |
|---|---|
| DNA | 100-500 ng |
| EcoRI | 5 units |

-continued

| MseI | 2 units |
|---|---|
| 5xRLbuffer | 8 μl |
| MilliQ water to | 40 μl |

Incubation was for 1 hour at 37° C. After the enzyme restriction, enzymes were inactivated by incubation for 10 minutes at 80° C.

Ligation of Adapters

| 10 mM ATP | 1 μl |
|---|---|
| T4 DNA ligase | 1 μl |
| EcoRI adaptor (5 pmol/μl) | 1 μl |
| MseI adaptor (50 pmol/μl) | 1 μl |
| 5xRLbuffer. | 2 μl |
| MilliQ water to | 40 μl |

Incubation was for 3 hours at 37° C.

Selective AFLP Amplification

Following restriction-ligation, the restriction/ligation reaction was diluted 10-fold with $T_{10}E_{0.1}$ and 5 μl diluted mix was used as a template in a selective amplification step. Note that since a +1/+2 selective amplification was intended, first a +1/+1 selective pre-amplification step (with standard AFLP primers) was performed. Reaction conditions of the +1/+1 (+A/+C) amplification were as follows.

| Restriction-Ligation mix (10-fold diluted) | 5 μl |
|---|---|
| EcoRI-primer + 1 (50 ng/μl): | 0.6 μl |
| MseI- primer + 1 (50 ng/μl) | 0.6 μl |
| dNTPs (20 mM) | 0.2 μl |
| Taq.polymerase (5 U/μl Amplitaq, PE) | 0.08 μl |

-continued

| 10XPCRbuffer | 2.0 μl |
|---|---|
| MilliQ water to | 20 μl |

Primers sequences were:

[SEQ ID NO: 9]
EcoRI + 1: 5'-AGACTGCGTACCAATTCA-3'
and

[SEQ ID NO: 10]
MseI + 1: 5'-GATGAGTCCTGAGTAAC-3'

PCR amplifications were performed using a PE9700 with a gold or silver block using the following conditions: 20 times (30 s at 94° C., 60 s at 56° C. and 120 s at 72° C.).

The quality of the generated +1/+1 preamplification products was checked on a 1% agarose gel using a 100 basepair ladder and a 1 Kb ladder to check the fragment length distribution. Following +1/+1 selective amplification, the reaction was diluted 20-fold with $T_{10}E_{0.1}$ and 5 μl diluted mix is used as a template in the +1/+2 selective amplification step using tagged AFLP primers.

Finally, +1/+2 (A/+CA) selective AFLP amplifications were performed:

| +1/+1 selective amplification product (20-fold diluted) | 5.0 μl |
|---|---|
| KRS EcoRI-primer + A (50 ng/μl) | 1.5 μl |
| KRS MseI- primer + CA (50 ng/μl) | 1.5 μl |
| dNTPs (20 mM) | 0.5 μl |
| Taq polymerase (5 U/μl Amplitaq, Perkin Elmer) | 0.2 μl |
| 10X PCR buffer | 5.0 μl |
| MQ to | 50 μl |

Tagged AFLP primers sequences were:

PSP11:

[SEQ ID NO: 1]
05F212: EcoRI + 1: 5'-<u>CGTC</u>AGACTGCGTACCAATTCA-3'
and

[SEQ ID NO: 2]
05F214: MseI + 2: 5'-<u>TGGT</u>GATGAGTCCTGAGTAACA-3'

PI201234:

[SEQ ID NO: 3]
05F213: EcoRI + 1: 5'-<u>CAAG</u>AGACTGCGTACCAATTCA-3'
and

[SEQ ID NO: 4]
05F215: MseI + 1: 5'-<u>AGCC</u>GATGAGTCCTGAGTAACA-3'

Note that these primers contain 4 bp tags (underlined above) at their 5 prime ends to distinguish amplification products originating from the respective pepper lines at the end of the sequencing process.

Schematic representation of pepper AFLP+1/+2 amplification products after amplification with AFLP primers containing 4 bp 5 prime tag sequences.

|  | EcoRI tag | MseI tag |
|---|---|---|
| PSP 11: | 5'-<u>CGTC</u> ------------------------------- | ACCA-3' |
|  | 3'-GCAG------------------------------------- | <u>TGGT</u>-5' |
| PI201234 | 5'-<u>CAAG</u> ------------------------------- | GGCT-3' |
|  | 3'-GTTC ------------------------------------- | <u>CCGA</u>-5' |

PCR amplifications (24 per sample) were performed using a PE9700 with a gold or silver block using the following conditions: 30 times (30 s at 94° C.+60 s at 56° C.+120 s at 72° C.).

The quality of the generated amplification products was checked on a 1% agarose gel using a 100 basepair ladder and a 1 Kb ladder to check the fragment length distribution.

AFLP Reaction Purification and Quantification.

After pooling two 50 microliter +1/+2 selective AFLP reactions per pepper sample, the resulting 12 100 μl AFLP reaction products were purified using the QIAquick PCR Purification Kit (QIAGEN), following the QIAquick® Spin handbook (Page 18). On each column a maximum of 100 μl product was loaded. Amplified products were eluted in $T_{10}E_{0.1}$. The quality of the purified products is checked on a 1% agarose gel and concentrations were measured on the NanoDrop® spectrophotometry (FIG. 2).

NanoDrop® spectrophotometry concentration measurements were used to adjust the final concentration of each purified PCR product to 300 nanograms per microliter. Five micrograms purified amplified product of PSP11 and 5 microgram of PI201234 were mixed to generate 10 microgram template material for preparation of the 454 sequencing library.

Sequence Library Preparation and High-Throughput Sequencing

Mixed amplification products from both pepper lines were subjected to high-throughput sequencing using 454 Life Sciences sequencing technology as described by Margulies et al., (Margulies et al., Nature 437, pp. 376-380 and Online Supplements). Specifically, the AFLP PCR products were first end-polished and subsequently ligated to adaptors to facilitate emulsion-PCR amplification and subsequent fragment sequencing as described by Margulies and co-workers. 454 adaptor sequences, emulsion PCR primers, sequence-primers and sequence run conditions were all as described by Margulies and co-workers. The linear order of functional elements in an emulsion-PCR fragment amplified on Sepharose beads in the 454 sequencing process was as follows as exemplified in FIG. 1A:

454 PCR adaptor-454 sequence adaptor-4 bp AFLP primer tag 1-AFLP primer sequence 1 including selective nucleotide(s)-AFLP fragment internal sequence-AFLP primer sequence 2 including selective nucleotide(s), 4 bp AFLP primers tag 2-454 sequence adaptor-454 PCR adaptor-Sepharose bead Two high-throughput 454 sequence runs were performed by 454 Life Sciences (Branford, Conn.; United States of America).

454 Sequence Run Data-Processing.

Sequence data resulting from 2 454 sequence runs were processed using a bio-informatics pipeline (Keygene N. V.). Specifically, raw 454 basecalled sequence reads were converted in FASTA format and inspected for the presence of tagged AFLP adaptor sequences using a BLAST algorithm. Upon high-confidence matches to the known tagged AFLP primer sequences, sequences were trimmed, restriction endonuclease sites restored and assigned the appropriate tags (sample 1 EcoRI (ES1), sample 1 MseI (MS1), sample 2 EcoRI (ES2) or sample 2 MseI (MS2), respectively). Next, all trimmed sequences larger than 33 bases were clustered using a megaBLAST procedure based on overall sequence homologies. Next, clusters were assembled into one or more contigs and/or singletons per cluster, using a CAP3 multiple alignment algorithm. Contigs containing more than one sequence were inspected for the sequence mismatches, representing putative polymorphisms. Sequence mismatches were assigned quality scores based on the following criteria:
 the numbers of reads in a contig
 the observed allele distribution
  The above two criteria form the basis for the so called Q score assigned to each putative SNP/indel. Q scores range from 0 to 1; a Q score of 0.3 can only be reached in case both alleles are observed at least twice.
 location in homopolymers of a certain length (adjustable; default setting to avoid polymorphism located in homopolymers of 3 bases or longer).
 number of contigs in cluster.
 distance to nearest neighboring sequence mismatches (adjustable; important for certain types of genotyping assays probing flanking sequences)
 the level of association of observed alleles with sample 1 or sample 2; in case of a consistent, perfect association between the alleles of a putative polymorphism and samples 1 and 2, the polymorphism (SNP) is indicated as an "elite" putative polymorphism (SNP). An elite polymorphism is thought to have a high probability of being located in a unique or low-copy genome sequence in case two homozygous lines have been used in the discovery process. Conversely, a weak association of a polymorphism with sample origin bears a high risk of having discovered false polymorphisms arising from alignment of non-allelic sequences in a contig.

Sequences containing SSR motifs were identified using the MISA search tool.

Overall statistics of the run is shown in the Table below.

TABLE

Overall statistics of a 454 sequence run for SNP discovery in pepper.

| Enzyme combination | Run |
|---|---|
| Trimming | |
| All reads | 254308 |
| Fault | 5293 (2%) |
| Correct | 249015 (98%) |
| Concatamers | 2156 (8.5%) |
| Mixed tags | 1120 (0.4%) |
| Correct reads | |
| Trimmed one end | 240817 (97%) |
| Trimmed both ends | 8198 (3%) |
| Number of reads sample 1 | 136990 (55%) |
| Number of reads sample 2 | 112025 (45%) |
| Clustering | |
| Number of contigs | 21918 |
| Reads in contigs | 190861 |
| Average number reads per contig | 8.7 |
| SNP mining | |
| SNPs with Q score ≥0.3 * | 1483 |
| Indel with Q score ≥0.3 * | 3300 |
| SSR mining | |
| Total number of SSR motifs identified | 359 |
| Number of reads containing one or more SSR motifs | 353 |
| Number of SSR motif with unit size 1 (homopolymer) | 0 |
| Number of SSR motif with unit size 2 | 102 |
| Number of SSR motif with unit size 3 | 240 |
| Number of SSR motif with unit size 4 | 17 |

Figure 7:
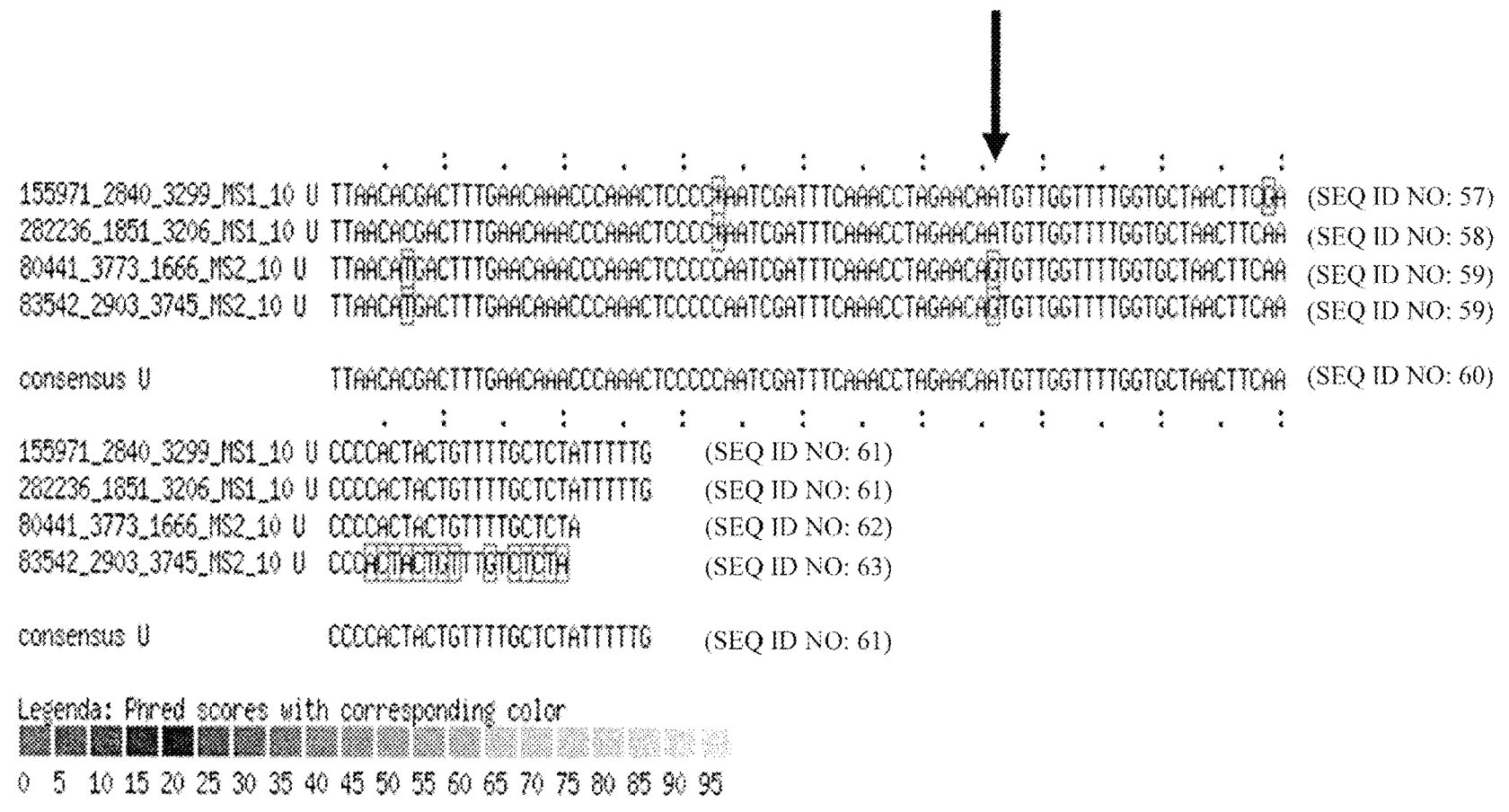

* SNP/indel mining criteria were as follows: No neighbouring polymorphisms with Q score larger than 0.1 within 12 bases on either side, not present in homopolymers of 3 or more bases. Mining criteria did not take into account consistent association with sample 1 and 2, i.e. the SNPs and indels are not necessarily elite putative SNPs/indels An example of a multiple alignment containing an elite putative single nucleotide polymorphism is shown in FIG. 7.

Example 5. SNP Validation by PCR Amplification and Sanger Sequencing

In order to validate the putative A/G SNP identified in example 1, a sequence tagged site (STS) assay for this SNP was designed using flanking PCR primers. PCR primer sequences were as follows:

```
Primer_1.2f:
                                             [SEQ ID NO: 37]
5'-AAACCCAAACTCCCCCAATC-3',
and Primer_1.2r:
                                             [SEQ ID NO: 38]
5'-AGCGGATAACAATTTCACACAGGACATCAGTAGTCACACTGGTACAA

AAATAGAGCAAAACAGTAGTG-3'
```

Note that primer 1.2r contained an M13 sequence primer binding site and length stuffer at its 5 prime end. PCR amplification was carried out using +A/+CA AFLP amplification products of PSP11 and PI210234 prepared as described in example 4 as template. PCR conditions were as follows:

For 1 PCR reaction the following components were mixed:
5 μl 1/10 diluted AFLP mixture (app. 10 ng/μl)
5 μl 1 pmol/μl primer 1.2f (diluted directly from a 500 μM stock)
5 μl 1 pmol/μl primer 1.2r (diluted directly from a 500 μM stock)
5 μl PCR mix—2 μl 10×PCR buffer
  1 μl 5 mM dNTPs
  1.5 μl 25 mM MgCl$_2$
  0.5 μl H$_2$O
5 μl Enzyme mix—0.5 μl 10×PCR buffer (Applied Biosystems)
  0.1 μl 5 U/μl AmpliTaq DNA polymerase (Applied Biosystems)
  4.4 μl H$_2$O The following PCR profile was used:

| | | |
|---|---|---|
| Cycle 1 | 2'; | 94° C. |
| Cycle 2-34 | 20"; | 94° C. |
| | 30"; | 56° C. |
| | 2'30"; | 72° C. |
| Cycle 35 | 7'; | 72° C. |
| | ∞; | 4° C. |

PCR products were cloned into vector pCR2.1 (TA Cloning kit; Invitrogen) using the TA Cloning method and transformed into INVαF' competent *E. coli* cells. Transformants were subjected to blue/white screening. Three independent white transformants each for PSP11 and PI-201234 were selected and grown 0/N in liquid selective medium for plasmid isolation.

Plasmids were isolated using the QIAprep Spin Miniprep kit (QIAGEN). Subsequently, the inserts of these plasmids were sequenced according to the protocol below and resolved on the MegaBACE 1000 (Amersham). Obtained sequences were inspected on the presence of the SNP allele. Two independent plasmids containing the PI-201234 insert and 1 plasmid containing the PSP11 insert contained the expected consensus sequence flanking the SNP. Sequence derived from the PSP11 fragment contained the expected A (underlined) allele and sequence derived from PI-201234 fragment contained the expected G allele (double underlined):

PSP11 (sequence 1): (5'-3')
[SEQ ID NO: 39]
AAACCCAAACTCCCCCAATCGATTTCAAACCTAGAACAATGTTGGTTTTG

GTGCTAACTTCAACCCACTACTGTTTTGCTCTATTTTTGT

PI-201234 (sequence 1): (5'-3')
[SEQ ID NO: 40]
AAACCCAAACTCCCCCAATCGATTTCAAACCTAGAACAGTGTTGGTTTTG

GTGCTAACTTCAACCCACTACTGTTTTGCTCTATTTTTG

PI-201234 (sequence 2): (5'-3')
[SEQ ID NO: 41]
AAACCCAAACTCCCCCAATCGATTTCAAACCTAGAACAGTGTTGGTTTTG

GTGCTAACTTCAACCCACTACTGTTTTGCTCTATTTTTG

This result indicates that the putative pepper A/G SNP represents a true genetic polymorphism detectable using the designed STS assay.

Example 6: SNP Validation by SNPWAve™ Detection

In order to validate the putative A/G SNP identified in example 1, SNPWAve™ ligation probes sets were defined for both alleles of this SNP using the consensus sequence. Sequence of the ligation probes were as follows:

SNPWAve™ probe sequences (5'-3'):
[SEQ ID NO: 42]
06A162 GATGAGTCCTGAGTAACCCAATCGATTTCAAACCTAGAACAA (42 bases)

[SEQ ID NO: 43]
06A163 GATGAGTCCTGAGTAACCACCAATCGATTTCAAACCTAGAACA

G (44 bases)

[SEQ ID NO: 44]
06A164 Phosphate-TGTTGGTTTTGGTGCTAACTTCAACCAACATCT

GGAATTGGTACGCAGTC (52 bases)

Note the allele specific probes 06A162 and 06A163 for the A and G alleles, respectively, differ by 2 bases in size, such that upon ligation to the common locus-specific probe 06A164, ligation product sizes of 94 (42+54) and 96 (44+52) bases result.

SNPWAve™ ligation and PCR reactions were carried as described by Van Eijk and co-workers (M. J. T. van Eijk, J. L. N. Broekhof, H. J. A. van der Poel, R. C. J. Hogers, H. Schneiders, J. Kamerbeek, E. Verstege, J. W. van Aart, H. Geerlings, J. B. Buntjer, A. J. van Oeveren, and P. Vos. (2004). SNPWAve™: a flexible multiplexed SNP genotyping technology. Nucleic Acids Research 32: e47), using 100 ng genomic DNA of pepper lines PSP11 and PI201234 and 8 ML offspring as starting material. Sequences of the PCR primers were:

[SEQ ID NO: 45]
93L01FAM (E00k): 5-GACTGCGTACCAATTC-3'

[SEQ ID NO: 46]
93E40 (M00k): 5-GATGAGTCCTGAGTAA-3'

Following PCR amplification, PCR product purification and detection on the MegaBACE1000 was as described by van Eijk and co-workers (vide supra). A pseudo-gel image of the amplification products obtained from PSP11, PI201234 and 8 ML offspring is shown in FIG. 8B.

The SNPWAve™ results demonstrate clearly that the A/G SNP is detected by the SNPWAve™ assay, resulting in 92 bp products (=AA homozygous genotype) for P1 (PSP11) and ML offspring 1, 2, 3, 4, 6 and 7), and in 94 bp products (=GG homozygous genotype) for P2 (PI201233) and RIL offspring 5 and 8.

Example 7: Strategies for Enriching AFLP Fragment Libraries for Low-Copy Sequences This example describes several enrichment methods to target low-copy of unique genome sequences in order to increase the yield of elite polymorphisms such as described in example 4. The methods can be divided into four categories:

1) Methods Aimed at Preparing High-Quality Genomic DNA, Excluding Chloroplast Sequences.

Here it is proposed to prepare nuclear DNA instead of whole genomic DNA as described in Example 4, to exclude co-isolation of abundant chloroplast DNA, which may result in reduced number of plant genomic DNA sequences, depending on the restriction endonucleases and selective AFLP primers used in the fragment library preparation process. A protocol for isolation of highly pure tomato nuclear DNA has been described by Peterson, D G., Boehm, K. S. & Stack S. M. (1997). Isolation of Milligram Quantities of Nuclear DNA From Tomato (*Lycopersicon esculentum*), A Plant Containing High Levels of Polyphenolic Compounds. Plant Molecular Biology Reporter 15 (2), pages 148-153.

2) Methods Aimed at Using Restriction Endonucleases in the AFLP Template Preparation Process which are Expected to Yield Elevated Levels of Low-Copy Sequences.

Here it is proposed to use certain restriction endonucleases in the AFLP template preparation process, which are expected to target low-copy or unique genome sequences, resulting in fragment libraries enriched for polymorphisms with increased ability to be convertible into genotyping assays. An examples of a restriction endonuclease targeting low-copy sequence in plant genomes is PstI. Other methylation sensitive restriction endonucleases may also target low-copy or unique genome sequences preferentially.

3) Methods Aimed a Selectively Removing Highly Duplicated Sequences Based on Reannealing Kinetics of Repeat Sequences Versus Low-Copy Sequences.

Here it is proposed to selectively remove highly duplicated (repeat) sequences from either the total genomic DNA sample or from the (cDNA-)AFLP template material prior to selective amplification.

3a) High-$C_0$t DNA preparation is a commonly used technique to enrich slowly annealing low-copy sequences from a complex plant genomic DNA mixture (Yuan et al. 2003; High-Cot sequence analysis of the maize genome. *Plant J.* 34: 249-255). It is suggested to take High-$C_0$t instead of total genomic DNA as starting material to enrich for polymorphisms located in low-copy sequences.

3b) An alternative to laborious high-$C_0$t preparation may be incubate denatured and reannealing dsDNA with a novel nuclease from the Kamchatka crab, which cleaves short, perfectly matched DNA duplexes at a higher rate than nonperfectly matched DNA duplexes, as described by Zhulidov and co-workers (2004; Simple cDNA normalization using Kamchatka crab duplex-specific nuclease. *Nucleic Acids Research* 32, e37) and Shagin and co-workers (2006; a novel method for SNP detection using a new duplex-specific nuclease from crab hepatopancreas. *Genome Research* 12: 1935-1942). Specifically, it is proposed to incubate AFLP restriction/ligation mixtures with this endonuclease to deplete the mixture of highly duplicated sequences, followed by selective AFLP amplification of the remaining low-copy or unique genome sequences.

3c) Methyl filtration is a method to enrich for hypomethylated genomic DNA fragments using the restriction endonuclease McrBC which cuts methylated DNA in the sequence [A/G]C, where the C is methylated (see Pablo D. Rabinowicz, Robert Citek, Muhammad A. Budiman, Andrew Nunberg, Joseph A. Bedell, Nathan Lakey, Andrew L. O'Shaughnessy, Lidia U. Nascimento, W. Richard McCombie and Robert A. Martienssen. Differential methylation of genes and repeats in land plants. Genome Research 15:1431-1440, 2005). McrBC may be used to enrich the low-copy sequence fraction of a genome as starting material for polymorphism discovery.

4) The Use of cDNA as Opposed to Genomic DNA in Order to Target Gene Sequences.

Finally, here it is proposed to use oligodT-primed cDNA as opposed to genomic DNA as starting material for polymorphism discovery, optionally in combination with the use the Crab duplex-specific nuclease described in 3b above for normalization. Note that the use of oligodT primed cDNA also excludes chloroplast sequences. Alternatively, cDNA-AFLP templates instead of oligodT primed cDNA is used to facilitate amplification of the remaining low-copy sequences in analogy to AFLP (see also 3b above).

Example 8: Strategy for Simple-Sequence Repeat Enrichment

This example describes the proposed strategy for discovery of Simple Sequence repeats sequences, in analogy to SNP discovery described in Example 4.

Specifically, Restriction-ligation of genomic DNA of two or more samples is performed, e.g. using restriction endonucleases PstI/MseI. Selective AFLP amplification is performed as described in Example 4. Next fragments containing the selected SSR motifs are enriched by one of two methods:

1) Southern blot hybridization onto filters containing oligonucleotides matching the intended SSR motifs (e.g. $(CA)_{15}$ in case of enrichment for CA/GT repeats), followed by amplification of bound fragments in a similar fashion as described by Armour and co-workers (Armour, J., Sismani, C., Patsalis, P., and Cross, G. (2000). Measurement of locus copy number by hybridization with amplifiable probes. Nucleic Acids Research vol 28, no. 2, pp. 605-609) or by 2) enrichment using biotinylated capture oligonucleotide hybridization probes to capture (AFLP) fragments in solution as described by Kijas and co-workers (Kijas, J. M, Fowler, J. C., Garbett C. A., and Thomas, M. R., (1994). Enrichment of microsatellites from the citrus genome using biotinylated oligonucleotide sequences bound to streptavidin-coated magnetic particles. Biotechniques, vol. 16, pp. 656-662.

Next, the SSR-motif enriched AFLP fragments are amplified using the same AFLP primers are used in the preamplification step, to generate a sequence library. An aliqout of the amplified fragments are T/A cloned and 96 clones are sequences to estimate the fraction of positive clones (clones containing the intended SSR motif, e.g. CA/GT motifs longer than 5 repeat units. Another aliquot of the enriched AFLP fragment mixture is detected by polyacrylamide gel electrophoresis (PAGE), optionally after further selective amplification to obtain a readable fingerprint, in order to visually inspect whether SSR containing fragments are enriched. Following successful completion of these control steps, the sequence libraries are subjected to high-throughput 454 sequencing.

Figure 8A:
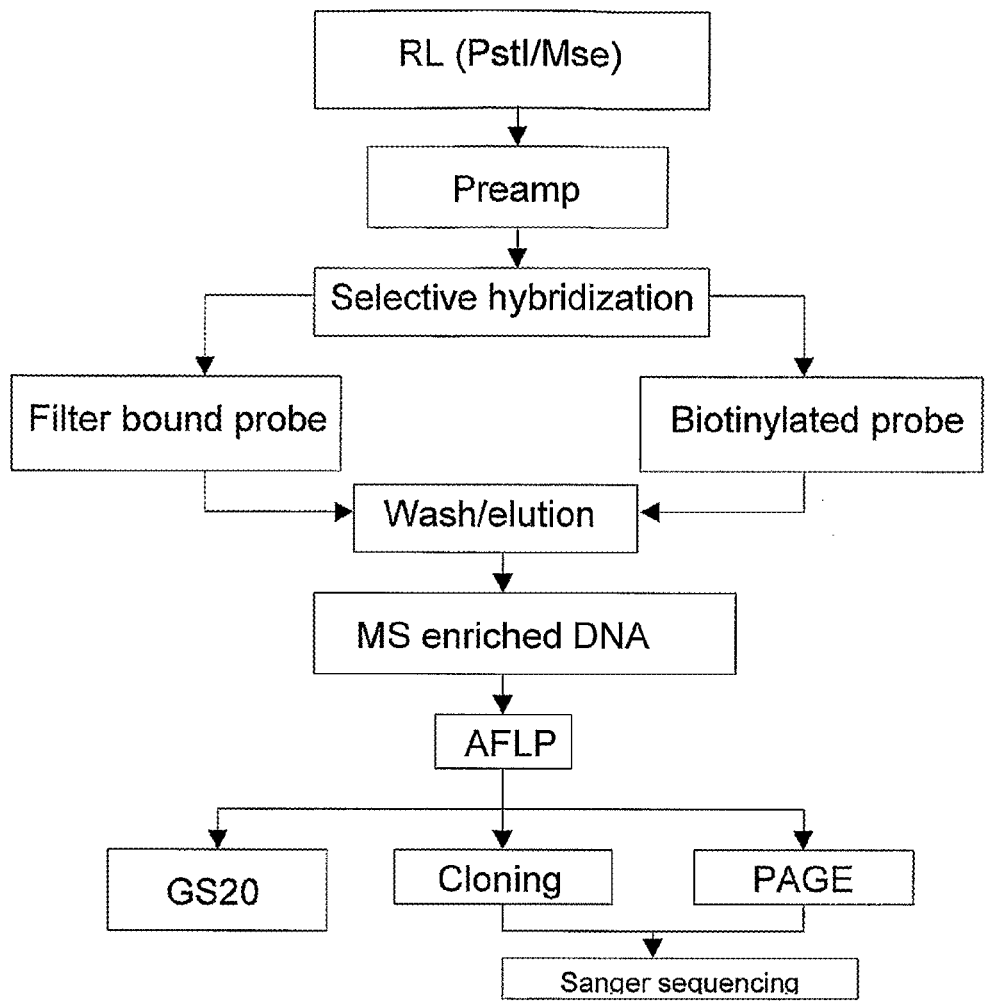
FIG. 8A. Schematic representation of enrichment strategy for targeting simple sequence repeats (SSRs) in combination with high throughput sequencing for de novo SSR discovery.
Figure 8B:
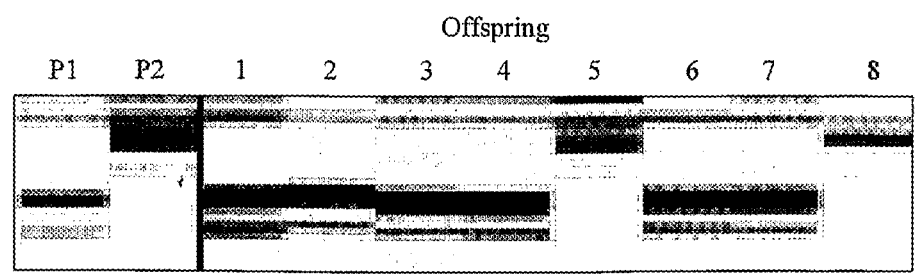
FIG. 8B: Validation of a G/A SNP in pepper using SNPWAve™ detection. P1=PSP11; P2=PI201234. Eight RIL offspring are indicated by numbers 1-8.

The above strategy for de novo SSR discovery is schematically depicted in FIG. 8A, and can be adapted for other sequence motifs by substituting the capture oligonucleotide sequences accordingly.

Example 9. Strategy for Avoiding Mixed Tags

Mixed tags refers to the observation that besides the expected tagged AFLP primer combination per sample, a low fraction of sequences are observed which contain a sample 1 tag at one end, and a sample 2 tag a the other end (See also the table 1 in example 4). Schematically, the configuration of sequences containing mixed tags is depicted here-in below.

Schematic Representation of the Expected Sample Tag Combinations.

```
          EcoRI tag                                    MseI tag

PSP 11:   5'-CGTC ---------------------------------- ACCA-3'
          3'-GCAG---------------------------------- TGGT-5'

PI-201234 5'-CAAG ---------------------------------- GGCT-3'
          3'-GTTC ---------------------------------- CCGA-5'
```

Schematic Representation of the Mixed Tags.

```
EcoRI tag                                      MseI tag

5'-CGTC ---------------------------------- GGCT-3'

3'-GCAG---------------------------------- CCGA-5'

5'-CAAG ---------------------------------- ACCA-3'

3'-GTTC ---------------------------------- TGGT-5'
```

The observation of mixed tags precludes correct assignment of the sequence to either PSP11 or PI-201234.

An example of a mixed tag sequence observed in the pepper sequence run described in Example 4 is shown in FIG. 5A. An overview of the configuration of observed fragments containing expected tags and mixed tags is shown in panel 2 of FIG. 5A.

The proposed molecular explanation for mixed tags is that during the sequence library preparation step, DNA fragments are made blunt by using T4 DNA polymerase or Klenow enzyme to remove 3 prime protruding ends, prior to adaptor ligation (Margulies et al., 2005). While this may work well when a single DNA sample is processed, in case of using a mixture of two or more samples differently tagged DNA samples, fill in by the polymerase results in incorporation of the wrong tag sequence in case when a heteroduplex has been formed between the complementary strands derived from different samples (FIG. 5B panel 3 mixed tags) The solution has been found to pool samples after the purification step that followed adaptor ligation in the 454 sequence library construction step as shown in FIG. 5C panel 4.

Example 10. Strategy for Avoiding Mixed Tags and Concatamers Using an Improved Design for 454 Sequence Library Preparation Besides the observation of low frequencies of sequence reads containing mixed tags as described in Example 9, a low frequency of sequence reads observed from concatenated AFLP fragments have been observed.

An example of a sequence read derived from a concatamer is shown in FIG. 6A Panel 1. Schematically, the configuration of sequences containing expected tags and concatamers is shown in FIG. 6A Panel 2.

The proposed molecular explanation for the occurrence of concatenated AFLP fragments is that during the 454 sequence library preparation step, DNA fragments are made blunt using T4 DNA polymerase or Klenow enzyme to remove 3 prime protruding ends, prior to adaptor ligation (Margulies et al., 2005). As a result, blunt end sample DNA fragments are in competition with the adaptors during the ligation step and may be ligated to each other prior to being ligated to adaptors. This phenomenon is in fact independent of whether a single DNA sample or a mixture of multiple (tagged) samples are included in the library preparation step, and may therefore also occur during the conventional sequencing as described by Margulies and co-workers. In case of the using multiple tagged samples as described in Example 4, concatamers complicate correct assignment of sequence reads to samples based on the tag information and are therefore to be avoided.

The proposed solution to the formation of concatamers (and mixed tags) is to replace blunt-end adaptor ligation with ligation of adaptors containing a 3 prime T overhang, in analogy to T/A cloning of PCR products, as shown in FIG. 6B Panel 3. Conveniently, these modified 3'prime T overhang-containing adaptors are proposed to contain a C overhang at the opposite 3'end (which will not be ligated to the sample DNA fragment, to prevent blunt-end concatamer formation of adaptor sequences (see FIG. 6B Panel 3). The resulting adapted workflow in the sequence library construction process when using the modified adaptor approach is shown schematically in FIG. 6C Panel 4.

The invention claimed is:

1. A kit for use in a method for detecting one or more polymorphisms in a plurality of nucleic acid samples, comprising: (a) an adaptor comprising a 3'-T overhang and (b) a set of primers for PCR amplification, wherein at least one of the adaptor and the primers comprises a sample-specific identifier sequence capable of indicating sample origin of an amplification product of the plurality of nucleic acid samples.

2. The kit according to claim 1, wherein the adaptor comprises the sample-specific identifier sequence.

3. The kit according to claim 1, wherein at least one of the primers comprises the sample-specific identifier sequence.

4. The kit according to claim 1, wherein the adaptor comprises a PCR primer-binding sequence for hybridizing to a PCR primer.

5. The kit according to claim 1, wherein the adaptor comprises a sequencing primer-binding sequence for hybridizing to a sequencing primer.

6. The kit according to claim 1, wherein the adaptor comprises sequences complementary to sequences attached to a solid support for annealing the adaptor to the solid support.

7. The kit according to claim 1, wherein the adaptor comprises sequences complementary to sequences attached to a bead for annealing the adaptor to the bead.

8. The kit according to claim 1, wherein at least one of the primers is phosphorylated.

9. The kit according to claim 1, wherein at least one of the primers comprises sequences at its 3'-end for hybridizing to a subset of nucleic acid sample fragments.

10. The kit according to claim 1, wherein the kit further comprises a biotinylated capture oligonucleotide hybridization probe for capturing a subset of nucleic acid sample fragments.

11. The kit according to claim 1, wherein the kit further comprises a polymerase for a polymerase chain reaction (PCR).

12. The kit according to claim 11, wherein the polymerase substantially lacks 3'-5' exonuclease activity.

* * * * *

SEQUENCE LISTING

<160> NUMBER OF SEQ ID NOS: 68

<210> SEQ ID NO 1
<211> LENGTH: 22
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 1
cgtcagactg cgtaccaatt ca                                               22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tggtgatgag tcctgagtaa ca                                               22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caagagactg cgtaccaatt ca                                               22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agccgatgag tcctgagtaa ca                                               22

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      adaptor oligonucleotide

<400> SEQUENCE: 5
ctcgtagact gcgtacc                                                     17

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      adaptor oligonucleotide

<400> SEQUENCE: 6
aattggtacg cagtctac                                                    18

<210> SEQ ID NO 7
<211> LENGTH: 16
<212> TYPE: DNA
<213> ORGANISM: Artificial Sequence
<220> FEATURE:
```

```
<223> OTHER INFORMATION: Description of Artificial Sequence: Synthetic
      adaptor oligonucleotide

<400> SEQUENCE: 7
gacgatgagt cctgag                                                         16

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: Synthetic
      adaptor oligonucleotide

<400> SEQUENCE: 8
tactcaggac tcat                                                           14

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agactgcgta ccaattca                                                       18

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gatgagtcct gagtaac                                                        17

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgtcagactg cgtaccaatt ca                                                  22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
caagagactg cgtaccaatt ca                                                  22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 13
tggtgatgag tcctgagtaa ca                                              22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agccgatgag tcctgagtaa ca                                              22

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gactgcgtac caattcaac                                                  19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gatgagtcct gagtaacag                                                  19

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgtcagactg cgtaccaatt ca                                              22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tggtgatgag tcctgagtaa ca                                              22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
caagagactg cgtaccaatt ca                                                22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agccgatgag tcctgagtaa ca                                                22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acgtgtagac tgcgtaccga aa                                                22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acgtgatgag tcctgagtaa ca                                                22

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgtagtagac tgcgtaccga ac                                                22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cgtagatgag tcctgagtaa ca                                                22

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 25
gtacgtagac tgcgtaccga ag                                              22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtacgatgag tcctgagtaa ca                                              22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tacggtagac tgcgtaccga at                                              22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tacggatgag tcctgagtaa ca                                              22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
agtcgtagac tgcgtaccga aa                                              22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agtcgatgag tcctgagtaa ca                                              22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
```
catggtagac tgcgtaccga ac                                              22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 32
catggatgag tcctgagtaa ca                                              22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 33
gagcgtagac tgcgtaccga ag                                              22

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 34
gagcgatgag tcctgagtaa ca                                              22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 35
tgatgtagac tgcgtaccga at                                              22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 36
tgatgatgag tcctgagtaa ca                                              22

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 37

```
aaacccaaac tcccccaatc                                                 20
```

```
<210> SEQ ID NO 38
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
agcggataac aatttcacac aggacatcag tagtcacact ggtacaaaaa tagagcaaaa    60
cagtagtg                                                              68

<210> SEQ ID NO 39
<211> LENGTH: 91
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
aaacccaaac tcccccaatc gatttcaaac ctagaacaat gttggttttg gtgctaactt    60 caacccact actgttttgc tctattttg t                                     91

<210> SEQ ID NO 40
<211> LENGTH: 90
<212> TYPE: DNA
<213> ORGANISM: Artificial Sequence
<220> FEATURE:
<223> OTHER INFORMATION: Description of Artificial Sequence: Synthetic
      PI-201234 SNP containing polynucleotide

<400> SEQUENCE: 40
aaacccaaac tcccccaatc gatttcaaac ctagaacagt gttggttttg gtgctaactt    60 caacccact actgttttgc tctattttg                                       90

<210> SEQ ID NO 41
<211> LENGTH: 90
<212> TYPE: DNA
<213> ORGANISM: Artificial Sequence
<220> FEATURE:
<223> OTHER INFORMATION: Description of Artificial Sequence: Synthetic
      PI-201234 SNP

<400> SEQUENCE: 41
aaacccaaac tcccccaatc gatttcaaac ctagaacagt gttggttttg gtgctaactt    60 caacccact actgttttgc tctattttg                                       90

<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence: Synthetic
      SNPWave probe

<400> SEQUENCE: 42
gatgagtcct gagtaaccca atcgatttca aacctagaac aa                       42

<210> SEQ ID NO 43
<211> LENGTH: 44
<212> TYPE: DNA
```

```
<213> ORGANISM: Artificial Sequence
<220> FEATURE:
<223> OTHER INFORMATION: Description of Artificial Sequence: Synthetic
      SNPWave probe

<400> SEQUENCE: 43
gatgagtcct gagtaaccac caatcgattt caaacctaga acag                      44

<210> SEQ ID NO 44
<211> LENGTH: 50
<212> TYPE: DNA
<213> ORGANISM: Artificial Sequence
<220> FEATURE:
<223> OTHER INFORMATION: Description of Artificial Sequence: Synthetic
      SNPWave probe

<400> SEQUENCE: 44
tgttggtttt ggtgctaact tcaaccaaca tctggaattg gtacgcagtc                50

<210> SEQ ID NO 45
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gactgcgtac caattc                                                     16

<210> SEQ ID NO 46
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gatgagtcct gagtaa                                                     16

<210> SEQ ID NO 47
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
taacacgact ttgaacaaac ccaaactccc ccaatcgatt tcaaacctag aacartgttg      60
gttttggtgc taacttcaac cccactactg ttttgctcta tttttg                   106

<210> SEQ ID NO 48
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
caagagactg cgtaccaatt caactttgag gtgaaagatc gaaggttgca                50

<210> SEQ ID NO 49
<211> LENGTH: 51
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
aacaccaagt ggccgaccat ctcttgcgtg ttactcagga ctcatcacca c        51

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tgttactcag gactcatcac ca                                        22

<210> SEQ ID NO 51
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tggtgatgag tcctgagtaa cgggcctttc tttgtacact                     40

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tggtgatgag tcctgagtaa ca                                        22

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tgaattggta cgcagtctga cg                                        22

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
agccgatgag tcctgagtaa ca                                        22

<210> SEQ ID NO 55
<211> LENGTH: 25
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 55
taaaggtaaa gcgtgaattg gtacg                                          25

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 56
tgaattggta cgcagtctct tg                                             22

<210> SEQ ID NO 57
<211> LENGTH: 80
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (33)..(33)
<223> OTHER INFORMATION: a, c, t, g, unknown or other

<400> SEQUENCE: 57
ttaacacgac tttgaacaaa cccaaactcc ccnaatcgat ttcaaaccta gaacaatgtt    60
ggttttggtg ctaacttcga                                                80

<210> SEQ ID NO 58
<211> LENGTH: 80
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (33)..(33)
<223> OTHER INFORMATION: a, c, t, g, unknown or other

<400> SEQUENCE: 58
ttaacacgac tttgaacaaa cccaaactcc ccnaatcgat ttcaaaccta gaacaatgtt    60
ggttttggtg ctaacttcaa                                                80

<210> SEQ ID NO 59
<211> LENGTH: 80
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 59
ttaacatgac tttgaacaaa cccaaactcc cccaatcgat ttcaaaccta gaacagtgtt    60
ggttttggtg ctaacttcaa                                                80

<210> SEQ ID NO 60
<211> LENGTH: 80
<212> TYPE: DNA

<213> ORGANISM: Artificial Sequence
<220> FEATURE:
<223> OTHER INFORMATION: Description of Artificial Sequence: Synthetic
    oligonucleotide

<400> SEQUENCE: 60
ttaacacgac tttgaacaaa cccaaactcc cccaatcgat ttcaaaccta gaacaatgtt    60
ggttttggtg ctaacttcaa    80

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 61
ccccactact gttttgctct atttttg    27

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 62
ccccactact gttttgctct a    21

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 63
cccactactg tttgtctcta    20

<210> SEQ ID NO 64
<211> LENGTH: 107
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<221> NAME/KEY: modified_base
<222> LOCATION: (33)..(33)
<223> OTHER INFORMATION: a, c, t, g, unknown or other

<400> SEQUENCE: 64
ttaacacgac tttgaacaaa cccaaactcc ccnaatcgat ttcaaaccta gaacaatgtt    60
ggttttggtg ctaacttcga ccccactact gttttgctct atttttg    107

<210> SEQ ID NO 65
<211> LENGTH: 107
<212> TYPE: DNA
<213> ORGANISM: Artificial Sequence
<220> FEATURE:

```
<223> OTHER INFORMATION: Description of Artificial Sequence: Synthetic
      polynucleotide
<220> FEATURE:
<221> NAME/KEY: modified_base
<222> LOCATION: (33)..(33)
<223> OTHER INFORMATION: a, c, t, g, unknown or other

<400> SEQUENCE: 65
ttaacacgac tttgaacaaa cccaaactcc ccnaatcgat ttcaaaccta gaacaatgtt        60
ggttttggtg ctaacttcaa ccccactact gttttgctct atttttg                    107

<210> SEQ ID NO 66
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
ttaacatgac tttgaacaaa cccaaactcc cccaatcgat ttcaaaccta gaacagtgtt        60
ggttttggtg ctaacttcaa ccccactact gttttgctct a                          101

<210> SEQ ID NO 67
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
ttaacatgac tttgaacaaa cccaaactcc cccaatcgat ttcaaaccta gaacagtgtt        60
ggttttggtg ctaacttcaa cccactactg tttgtctcta                            100

<210> SEQ ID NO 68
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
ttaacacgac tttgaacaaa cccaaactcc cccaatcgat ttcaaaccta gaacaatgtt        60
ggttttggtg ctaacttcaa ccccactact gttttgctct atttttg                    107
```